(12) United States Patent
Fujimaki et al.

(10) Patent No.: US 9,269,118 B2
(45) Date of Patent: Feb. 23, 2016

(54) DEVICE, METHOD, AND PROGRAM FOR EXTRACTING ABNORMAL EVENT FROM MEDICAL INFORMATION

(75) Inventors: Ryohei Fujimaki, Tokyo (JP); Satoshi Morinaga, Tokyo (JP)

(73) Assignee: NEC CORPORATION, Tokyo (JP)

( * ) Notice: Subject to any disclaimer, the term of this patent is extended or adjusted under 35 U.S.C. 154(b) by 301 days.

(21) Appl. No.: 13/806,939

(22) PCT Filed: Jun. 23, 2011

(86) PCT No.: PCT/JP2011/003587
§ 371 (c)(1),
(2), (4) Date: Mar. 8, 2013

(87) PCT Pub. No.: WO2012/001920
PCT Pub. Date: Jan. 5, 2012

(65) Prior Publication Data
US 2013/0166572 A1     Jun. 27, 2013

(30) Foreign Application Priority Data
Jun. 28, 2010   (JP) ................................ 2010-146680

(51) Int. Cl.
G06F 17/30     (2006.01)
G06Q 50/22    (2012.01)
G06Q 10/00    (2012.01)

(52) U.S. Cl.
CPC .......... *G06Q 50/22* (2013.01); *G06F 17/30312* (2013.01); *G06Q 10/00* (2013.01)

(58) Field of Classification Search
None
See application file for complete search history.

(56) References Cited

U.S. PATENT DOCUMENTS

2011/0082867 A1*   4/2011   Bruns et al. ................... 707/748

FOREIGN PATENT DOCUMENTS

| JP | 2002-15061 A | 1/2002 |
| JP | 2002-342484 A | 11/2002 |
| JP | 2007-122418 A | 5/2007 |

OTHER PUBLICATIONS

Yasuhide Miura, et al., "Denshi Karute kara no Fukusayo Kankei no Jido Chushutsu", Proceedings of the 16th annual meeting of the Association for Natural Language Processing, Mar. 8, 2010, pp. 78-81.

"Study result report on introduction of data mining technique", Pharmaceuticals and Medical Devices Agency, online, searched May 21, 2010, <URL: http://www.info.pdma.go.jp/kyoten_iyaku/file/dm-report20.pdf>.

* cited by examiner

*Primary Examiner* — Anh Tai Tran
(74) *Attorney, Agent, or Firm* — Sughrue Mion, PLLC

(57) ABSTRACT

An abnormality score calculating means calculates abnormality scores which are information indicating abnormality of medical data, based on specificity of the medical data. An abnormality score vector generating means creates at least one or more abnormality score vectors which are information obtained by integrating the abnormality scores. Further, a side effect detecting means which decides a likelihood of a side effect indicated by the abnormality score vector, based on a predetermined rule, and detects an abnormality score vector the likelihood of which is set in advance and which satisfies conditions as information indicating the side effect.

11 Claims, 12 Drawing Sheets

DEVICE, METHOD, AND PROGRAM FOR EXTRACTING ABNORMAL EVENT FROM MEDICAL INFORMATION

CROSS REFERENCE TO RELATED APPLICATIONS

This application is a National Stage of International Application No. PCT/JP2011/003587 filed Jun. 23, 2011, claiming priority based on Japanese Patent Application No. 2010-146680 filed Jun. 28, 2010, the contents of all of which are incorporated herein by reference in their entirety.

TECHNICAL FIELD

This invention relates to a device, method and program which extract an abnormal event from medical information.

BACKGROUND ART

In many cases, drugs which are available in a market cause side effects which could not be found by inspection upon development. Hence, doing researches to quickly find side effects which occur in the market and managing side effect information are important to manage safety of drugs and improve the drugs.

Currently, when a drug causes a side effect, each medical organization needs to report the side effect to, for example, a government. When a side effect is reported, this information is accumulated in a side effect report database (side effect DB). It is difficult for people to check and process all reports on side effects accumulated in the side effect DB, and therefore methods of specifying a side effect of a drug from these reports are being proposed.

Non Patent Literature 1 discloses a method of detecting a pair of a drug and a side effect by using methods such as Bayesian Confidence Propagation Neural Network, Gamma-Poisson Shrinker and Reporting Odds Ratio. According to the method disclosed in Non Patent Literature 1, information including a pair of "drug-side effect" is automatically extracted from the side effect DB in which an enormous amount of information is stored, and a side effect of a drug is detected based on the event probability of this pair.

Further, Patent Literature 1 discloses a clinical trial managing system which comprehensively manages clinical trials. The system disclosed in Patent Literature 1 has a set exclusion criterion indicating, for example, an abnormal value of data or occurrence of a side effect. Further, whether or not a side effect occurs is decided based on whether or not an abnormal value is produced or a doctor's opinion.

Furthermore, Patent Literature 2 discloses a method of identifying and predicting a drug side effect. According to the method disclosed in Patent Literature 2, an ADE (Adverse Drug Events) rule is defined in advance. Further, when a test value is not included in a range of a normal test value in the ADE rule, the test value is decided to be abnormal and warning processing is performed.

CITATION LIST

Patent Literature

PTL 1: Patent 2002-15061
PTL 2: Patent 2002-342484

Non Patent Literature

NPL 1: Pharmaceuticals and Medical Devices Agency "Study result report on introduction of data mining technique", [online], [searched on May 21, 2010, Internet <URL:http://www.info.pmda.go.jp/kyoten_iyaku/file/dm-report20.pdf>

SUMMARY OF INVENTION

Technical Problem

Both of the system disclosed in Patent Literature 1 and the method disclosed in Patent Literature 2 are directed to detecting abnormality by comparing rules determined in advance and test values. In other words, neither the system disclosed in Patent Literature 1 nor the method disclosed in Patent Literature 2 cannot detect abnormality in relation to the rule determined in advance. Therefore, it is difficult to detect a latent abnormality for an unknown rule which is not yet defined.

Further, when a side effect of a drug is detected by the method disclosed in Non Patent Literature 1, there is a problem that an unknown side effect which is not reported cannot be detected. When, for example, a time is required until a side effect is reflected in the side effect DB after the side effect is found in the market, detection of the side effect is delayed.

It is therefore an exemplary object of this invention to provide a device, a method and a program which extract an abnormal event from medical information and which can extract an unknown side effect of a drug from information related to medical treatment.

Solution to Problem

A device which extracts an abnormal event from medical information according to this invention has: an abnormality score calculating means which calculates an abnormality score which is information indicating abnormality of medical data, based on specificity of the medical data; an abnormality score vector generating means which creates at least one or more abnormality score vectors which are information obtained by integrating the abnormality score; and a side effect detecting means which decides a likelihood of a side effect indicated by the abnormality score vector, based on a predetermined rule, and detects an abnormality score vector the likelihood of which satisfies a condition set in advance as information indicating the side effect.

A method of extracting an abnormal event from medical information according to this invention includes: calculating an abnormality score which is information indicating abnormality of medical data, based on specificity of the medical data; creating at least one or more abnormality score vectors which are information obtained by integrating the abnormality score; and deciding a likelihood of a side effect indicated by the abnormality score vector, based on a predetermined rule, and detecting an abnormality score vector the likelihood of which satisfies a condition set in advance as information indicating the side effect.

A program of extracting an abnormal event from medical information according to this invention causes a computer to execute: abnormality score calculation processing of calculating an abnormality score which is information indicating abnormality of medical data, based on specificity of the medical data; abnormality score vector creation processing of creating at least one or more abnormality score vectors which are information obtained by integrating the abnormality score; and side effect detection processing of deciding a likelihood of a side effect indicated by the abnormality score vector, based on a predetermined rule, and detecting an abnormality score vector the likelihood of which satisfies a condition set in advance as information indicating the side effect.

Advantageous Effects of Invention

This invention can extract an unknown side effect of a drug from information related to medical treatment.

DESCRIPTION OF EMBODIMENTS

Hereinafter, exemplary embodiments of this invention will be described with reference to the drawings. In addition, in the following description, side effect information reports, charts, receipts, health diagnosis information and DPC (Diagnosis Procedure Combination) including information related to medical treatment will be collectively referred to as "medical information".

Medical information includes a plurality of items of data, and each data is vector data including a plurality of items related to medical treatment. Meanwhile, when the number of items is Dx, n-th data of medical information is referred to as "xn=(xn1, . . . , xnDx)". Further, each item in the data xn is also referred to as "xnd".

Each item xnd in the data xn can take an arbitrary value (for example, a real value, a discrete value or a symbol value). The item xnd is, for example, a symbol value such as a name of an administered drug or a sex, a real value such as the amount of a drug or a test value in a blood test or a discrete value such as the number of times of administration of a drug, an age or a medical expense.

Further, whether or not a side effect occurs in the data xn or information indicating seriousness (referred to as "side effect/seriousness information") is referred to as "yn=(yn1, . . . , ynDy)". Meanwhile, Dy indicates the number of items of side effect/seriousness information. In addition, each information in the side effect/seriousness information yn is also referred to as "ynd".

Each information ynd indicating whether or not a side effect occurs or seriousness can take an arbitrary value. The side effect/seriousness information ynd is, for example, a symbol value indicating whether or not a side effect occurs, a discrete value representing seriousness of the side effect or a real value representing seriousness of the side effect.

Further, a data sequence of a length N in the data xn is defined as "x^N=x1, . . . , xN", and a data sequence of the length N in the side effect/seriousness information yn is defined as "y^N=y1, . . . , yN".

First Exemplary Embodiment

Figure 1:
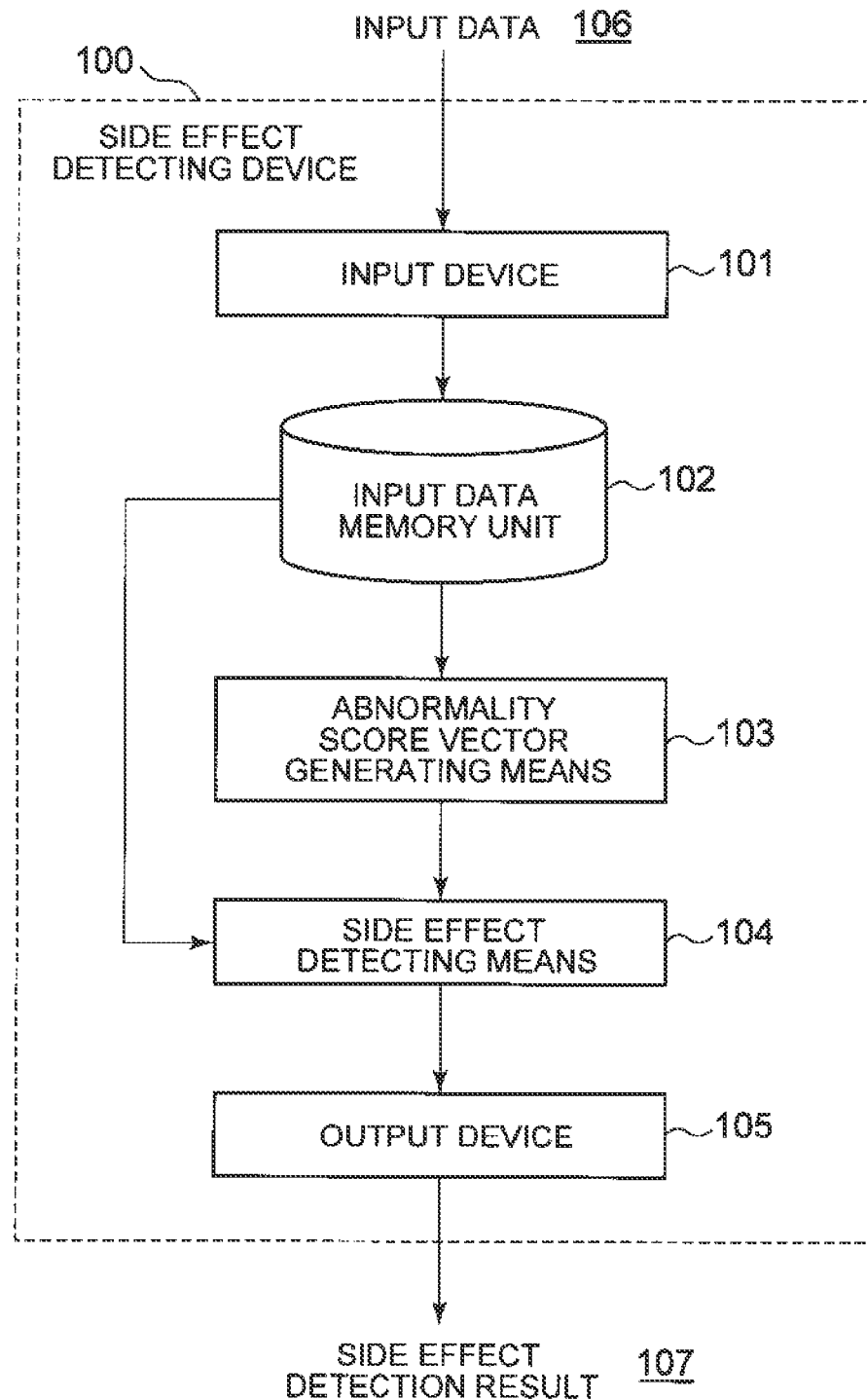
FIG. 1 It depicts a block diagram illustrating an example of a side effect detecting device according to a first exemplary embodiment of this invention.

FIG. 1 is a block diagram illustrating an example of a device (hereinafter, referred to as a "side effect detecting device" below in description of each exemplary embodiment) which extracts an abnormal event from medical information according to a first exemplary embodiment of this invention. A side effect detecting device 100 according to this exemplary embodiment has an input device 101, an input data memory unit 102, an abnormality score vector generating means 103, a side effect detecting means 104 and an output device 105. The input device 101 receives an input of input data 106. Further, the output device 105 outputs a side effect detection result 107.

The input device 101 is a device for receiving an input of the input data 106. The input device 101 has the input data memory unit 102 store the input data 106 received from, for example, an external device.

Meanwhile, the input data 106 includes data required for an operation of the side effect detecting device 100 such as parameters required for subsequent analysis processing in addition to medical information and information indicating whether or not a side effect occurs in the data xn and seriousness (that is, the side effect/seriousness information yn).

The input data memory unit 102 stores the input data 106. The input data memory unit 102 is realized by, for example, a magnetic disk.

Figure 2:
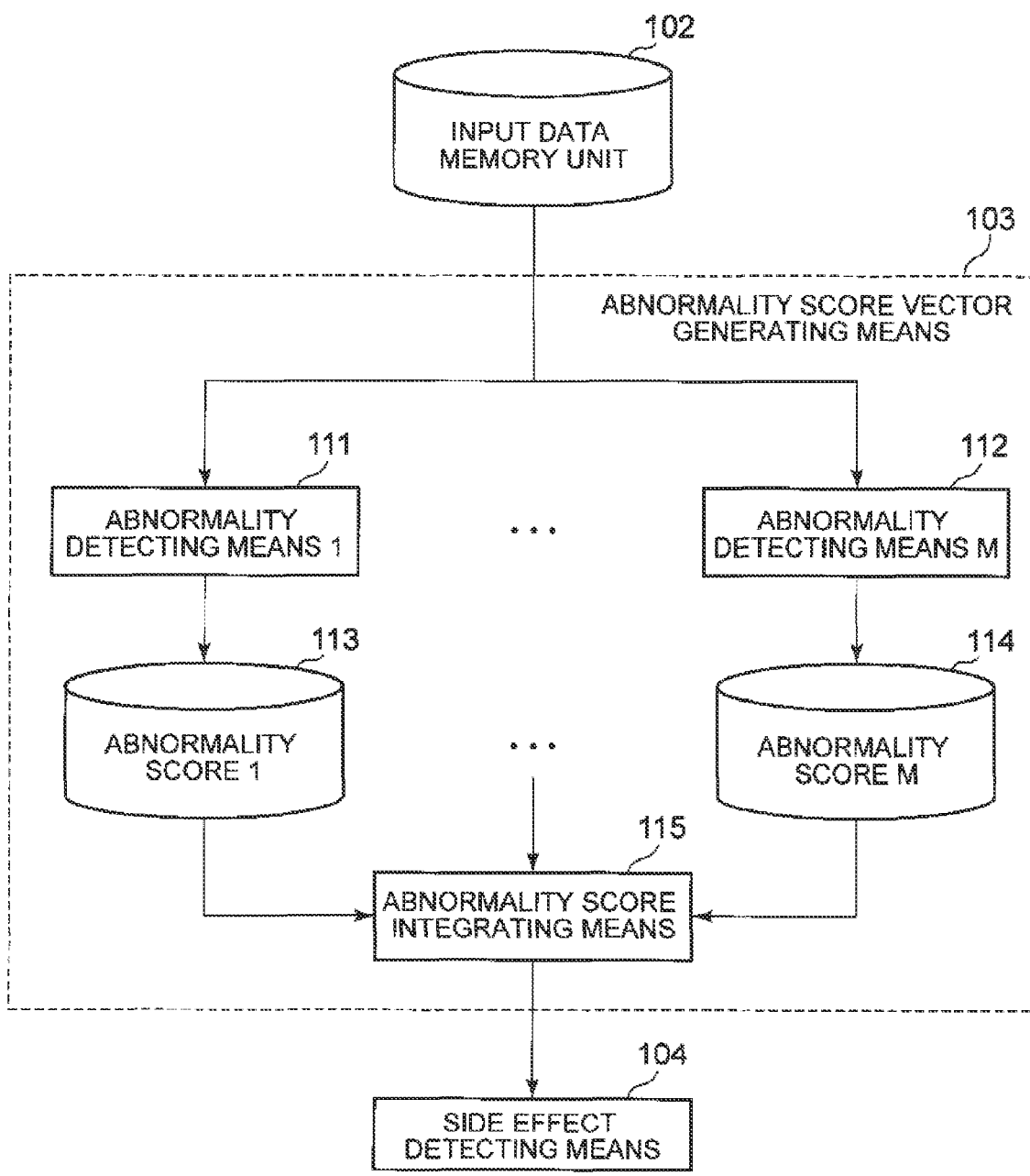
FIG. 2 It depicts an explanatory view illustrating an example of an abnormality score vector generating means 103.

FIG. 2 is an explanatory view illustrating an example of the abnormality score vector generating means 103 according to this exemplary embodiment. The abnormality score vector generating means 103 has an abnormality detecting means 1_111 to an abnormality detecting means M_112 (referred to as an "abnormality detecting means" below), and an abnormality score integrating means 115. Meanwhile, M represents the number of abnormality detecting means. In addition, M is an integer equal to or more than 1. Each abnormality detecting means calculates an abnormality score 1_113 to an abnormality score M_114 (referred to as an "abnormality score" below) which are scores calculated as a result of abnormality detection based on medical information of the input data 106. Further, the abnormality score integrating means 115 generates an abnormality score vector based on a plurality of calculated abnormality scores. Meanwhile, the abnormality score vector is information obtained by integrating each abnormality score calculated by the abnormality detecting means. Hereinafter, operations of the abnormality detecting means and the abnormality score integrating means 115 will be described in detail.

The abnormality detecting means calculates the abnormality score of each data xn of medical information by using an arbitrary abnormality detecting method. More specifically, the abnormality detecting means calculates the abnormality score of each data xn based on specificity indicated by each data xn of medical information. The abnormality score is, more specifically, information representing abnormality of each data xn, and is represented in an arbitrary format such as a real value which indicates higher abnormality when the real value is higher, a discrete value indicating whether or not abnormality occurs or a symbol value representing the type or the degree of abnormality. A specific example of the abnormality score is a score representing an outlier, a score representing a change point or a score representing a likelihood of a side effect when supervised learning is utilized. Further, the abnormality score also includes a value indicating whether or not there is a predetermined pattern indicating abnormality (for example, 1 when there is a predetermined pattern and 0 when there is not a predetermined pattern).

A specific example of the abnormality detecting method is an outlier detecting technique, a change point detecting technique, a classifying technique, a regressing technique or a method of deciding whether or not data matches with a specific rule. The outlier detecting technique refers to a technique of extracting specific information from time-series data of the same kind. For example, data [x1, x2, . . . , x10] is receipt data related to administration of a given drug. Meanwhile, a technique of, when only x2 indicates that a medical expense is unusually high, extracting this x2 is the outlier detecting technique. Further, the outlier detecting technique also includes a method of handling the data xn (or part thereof) as a multidimensional vector and performing cross-sectional outlier detection of a plurality of items of data of x^N.

The change point detecting technique refers to a technique of detecting a point at which there is a rapid change in time-series data. For example, data [x1, x2, x3] is temporally continuous receipt data related to administration of a given drug. A technique of detecting a rapid decrease in the amount of a drug or a rapid increase in the amount of another drug under such a situation is the change point detecting technique.

Further, the classifying technique is a technique of classifying other data based on a classification model. The classifying technique is, for example, a method of creating a classification model using the data x^N indicating whether or not a given effect occurs as y^N, and deciding whether or not a side effect occurs in the rest of items of data based on this classification model. The regressing technique refers to a technique of deciding other data based on a regression model. The regressing technique is, for example, a method of creating a regression model using the data x^N including seriousness of a given side effect as y^N, and deciding the seriousness of the side effect in the rest of items of data based on this regression model.

Whether or not data matches with a specific rule may be decided by deciding, for example, whether or not the data xn matches with a specific rule that, "when urgent medical treatment is performed immediately after administration of a given drug, the probability of the side effect is high".

In addition, a method (for example, outlier detection) of calculating data (for example, receipt data related to administration of a drug) and an abnormality score which are targets of abnormality detection processing performed by the abnormality detecting means is determined in advance per abnormality detecting means.

In the following description, one of the abnormality detecting means is an abnormality detecting means m, and the number of abnormality scores calculated by the abnormality detecting means m for the data x^N is Km. In this case, the abnormality scores calculated by the abnormality detecting means m is referred to as "smk (where k=1, . . . , Km)". Further, an index vector of the data xn linked to the abnormality scores smk is referred to as "tmk=(tmk1, . . . , tmkN)". Meanwhile, when an element of the index vector is tmkn, tmkn=1 represents that smk and xn are linked, and tmkn=0 represents that smk and xn are not linked.

However, the correspondence between an abnormality score and the data xn is not limited to a one-to-one correspondence. One abnormality score may be linked to a plurality of items of data xn. That is, a plurality of elements in the index vector tmk may be 1. More specifically, the abnormality detecting means m calculates one abnormality score for a plurality of items of data xn in this case. For example, data [x1, x2, x3] is temporally continuous data about a given person. Meanwhile, when the abnormality detecting means m detects abnormality for a d-th dimensional sequence [x1d→x2d→x3d], one abnormality score is calculated for the data [x1, x2, x3].

The abnormality score integrating means 115 creates information (that is, an abnormality score vector) obtained by integrating abnormality scores calculated by each abnormality detecting means. More specifically, when the abnormality score vector is wi, the dimension of the abnormality score vector is Dw and the number of abnormality score vectors to be output is Nw, the abnormality score integrating means 115 creates an abnormality score vector wi=(wi1, . . . , wiDw) by integrating the abnormality score 1_113 (s11, . . . , s1K1) to the abnormality score M_114 (sM1, . . . , sMKM) by using an arbitrary method. Meanwhile, i=1, . . . , Nw is true. Further, the abnormality score integrating means 115 also generates an index vector (referred to as "ui" below) of the abnormality score linked to the abnormality score vector wi. In addition, in the following description, the abnormality score vectors created by the abnormality score integrating means 115 are also represented as "w^Dw=w1, . . . , wDw".

The abnormality score integrating means 115 may configure the abnormality score vector wi by, for example, arranging the abnormality scores linked to the data xn as vectors. In addition, other methods of creating abnormality score vectors will be described below.

The side effect detecting means 104 detects the side effect of each data included in medical information. More specifically, the side effect detecting means 104 detects a side effect of w^Dw by using an arbitrary method. The side effect detecting means 104 may detect data indicated by an abnormality score vector of higher abnormality as side effect data from, for example, the abnormality score vectors created by the abnormality score integrating means 115 as information indicating the side effect. Further, the side effect detecting means 104 may present abnormality score vectors in order of a higher likelihood indicating a side effect upon comparison with predetermined conditions.

For example, the side effect detecting means 104 may calculate the likelihood of the side effect as the weighted sum (referred to as a "side effect score" below) of the abnormality score vectors wi, and present abnormality score vectors in a ranking format of the side effect scores. Further, the side effect detecting means 104 may detect an abnormality score vector having a higher side effect score than a predetermined threshold as information indicating the side effect. In addition, data linked to the abnormality score vector wi can be specified by referring to the index vector ui of the abnormality score linked to the abnormality score vector wi and the index vector tmk of the data xn.

In addition, the side effect detecting means 104 may learn an abnormality score vector linked to data indicating the side effect, and a classification model of an abnormality score vector linked to data without the side effect. In this case, the side effect detecting means 104 may decide whether or not a side effect occurs (likelihood) in the rest of items of data based on this classification model.

Meanwhile, a specific operation of the method of learning the above classification model will be described. First, the side effect detecting means 104 labels each of Dw abnormality score vectors based on the linked input data. By so doing, it is possible to obtain, for example, results of abnormality score vectors w1, w2 and w3 that the abnormality score vector w1 indicates that "a side effect occurs", the abnormality score vector w2 indicates that a side effect does not occur and the abnormality score vector w3 indicates that whether or not a side effect occurs is not linked. Next, the side effect detecting means 104 learns a classification model for deciding whether or not a side effect occurs using an abnormality score vector labeled as "a side effect occurs" and an abnormality score vector labeled as "a side effect does not occur". The classification model is arbitrary, and is, for example, a logistic regression model, a naive Bayes model or a decision tree. Next, the side effect detecting means 104 decides whether or not a side effect of an abnormality score vector which is not liked with whether or not a side effect occurs using the learned classification model.

In addition, a case has been described with this example where a learning method based on supervised learning is used as described above. Meanwhile, the learning method utilized by the side effect detecting means 104 is by no means limited to the supervised learning. The side effect detecting means 104 may utilize a semi-supervised learning method of learning a classification model by, for example, simultaneously utilizing data which is labeled with whether or not a side effect occurs and data which is not labeled with whether or not a side effect occurs. The semi-supervised classification learning is, for example, a Lhaplus support vector machine.

Further, the side effect detecting means 104 may learn a regression model of seriousness for an abnormality score vector linked to data indicating a side effect and an abnormality score vector linked to data without a side effect. In this case, the side effect detecting means 104 may extract an abnormality score vector which has a conditional expected value equal to or more than a predetermined value, based on this regression model.

In addition, the side effect detecting means 104 reads input data linked to the abnormality score vector from the input data memory unit 102 when necessary to utilize to detect a side effect. When, for example, there is a difference in the incidence rate of a side effect depending on the sex and the age, the side effect detecting means 104 may read information indicating the sex and the age from the input data memory unit 102 and utilize the read information to detect the side effect. Thus, by utilizing data of the input data memory unit 102 linked to the abnormality score vector, it is possible to improve precision to detect a side effect.

Further, the side effect detecting means 104 may create a basic statistical amount of the data xn as a detection result of the side effect. The statistical amount of the data xn is, for example, the male-to-female ratio, the age ratio, a distribution of heights and weights, a distribution of administered drugs and an average value and dispersion of medical expenses of input data linked to the abnormality score vector which is suspected to indicate a side effect.

A case has been described above where the abnormality score integrating means 115 creates one type of an abnormality score vector according to a given specific calculating method, and the side effect detecting means 104 detects the side effect for the created abnormality score vector. Meanwhile, the abnormality score vector created by the abnormality score integrating means 115 is not limited to one type. Further, the number of the side effect detecting means 104 may be plural instead of one.

Figure 3:
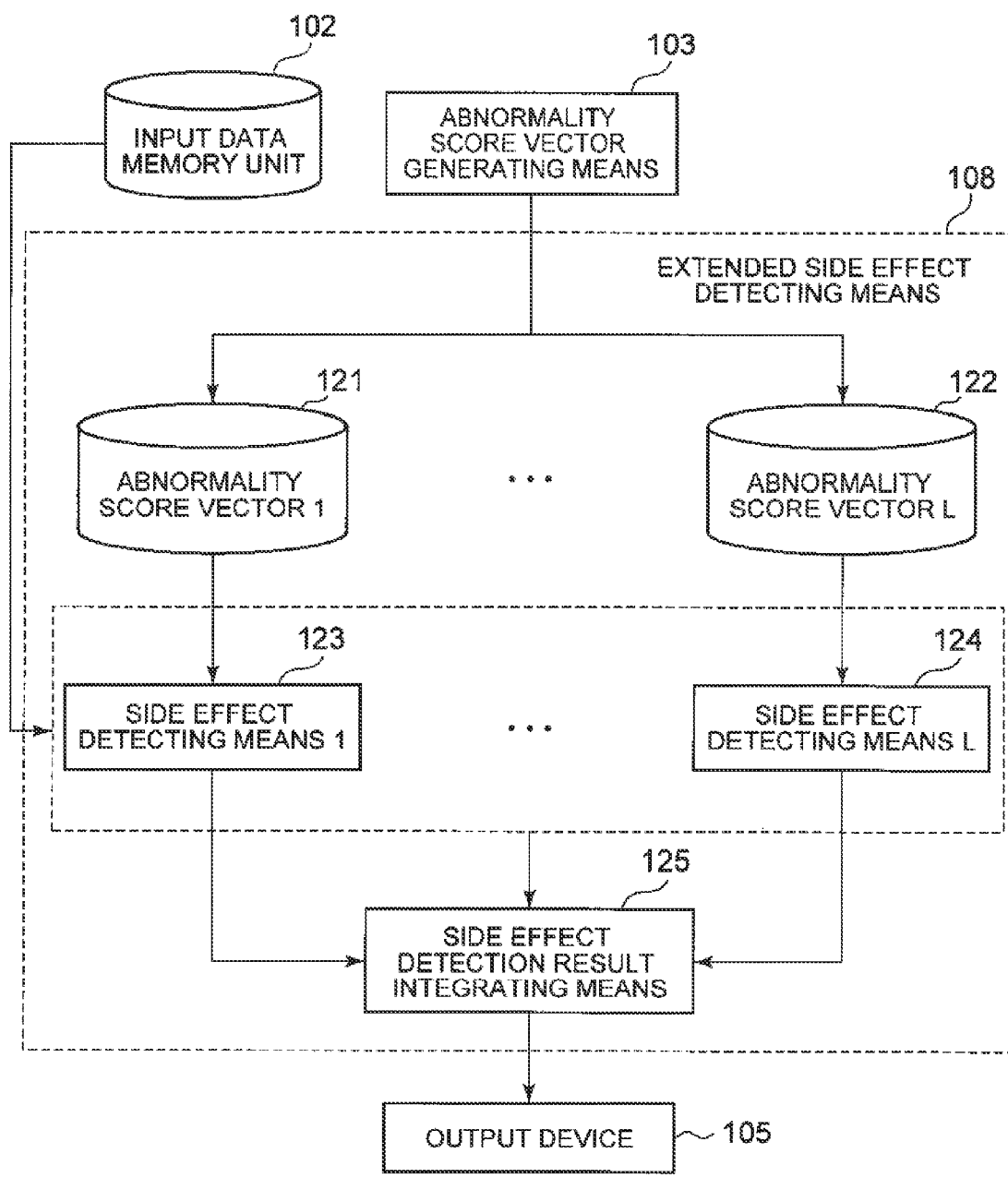
FIG. 3 It depicts an explanatory view illustrating another example of a side effect detecting means.

FIG. 3 is an explanatory view illustrating another example of a side effect detecting means. An extended side effect detecting means 108 illustrated in FIG. 3 has a side effect detecting means 1_123 to a side effect detecting means L_124, and a side effect detection result integrating means 125. Meanwhile, L refers to the number of side effect detecting means. Further, the abnormality score vector generating means 103 creates L types of abnormality score vector 1_121 to an abnormality score vector L_122.

Each of the side effect detecting means 1_123 to the side effect detecting means L_124 detects a side effect according to an arbitrary method based on a corresponding abnormality score vector created by the abnormality score integrating means 115. In addition, a method each of the side effect detecting means 1_123 to the side effect detecting means L_124 to detect the type of a target abnormality score vector and a side effect may be determined in advance. Further, when the abnormality score integrating means 115 creates the L types of abnormality score vectors, by determining information about the abnormality score vector utilized by each of the side effect detecting means 1_123 to the side effect detecting means L_124 in advance, the abnormality score integrating means 115 only needs to create the abnormality score vector based on this information. In this case, a method of creating an abnormality score vector is arbitrary per abnormality score vector 1_121 to abnormality score vector L_122, and each method may be different or identical.

Further, in this case, the abnormality score integrating means 115 may not only create abnormality score vectors by simply converting abnormality scores into vectors, but also create abnormality score vectors by taking cross terms (two or more multiplication terms) of the abnormality scores 1 to M. In addition, the abnormality score integrating means 115 may generate an abnormality score vector by applying projection such as main component analysis to a vector obtained by arranging abnormality scores. In addition, a projection method may vary between the abnormality score vector 1 and the abnormality score vector L.

The side effect detection result integrating means 125 integrates side effect detection results of the side effect detecting means 1_123 to the side effect detecting means L_124, and generates a final side effect detection result. More specifically, the side effect detection result integrating means 125 generates a final side effect detection result based on L decision values (for example, binary values or decision function values indicating whether or not sides effects are suspected to occur) outputted as side effect detection results (referred to as "side effect detection results 1 to L" below) of each of the side effect detecting means 1_123 to the side effect detecting means L_124.

For example, the side effect detection result integrating means 125 may calculate a weighted sum of the L decision values, and present calculation results in the ranking format. Further, the side effect detection result integrating means 125 may learn the function representing a likelihood of a side effect utilizing a vector obtained by arranging the L decision values output as the side effect detection results 1 to L and a corresponding label of a side effect. Meanwhile, in this case, a side effect label may not be included in all vectors.

In view of above, upon comparison between the side effect detecting means 104 illustrated in FIG. 2 and the extended side effect detecting means 108 illustrated in FIG. 3, the side effect detecting means 104 creates an abnormality score vector according to a given specific calculating method and detects a side effect of this abnormality score vector. Meanwhile, the extended side effect detecting means 108 detects a side effect of each abnormality score vectors created by the side effect detecting means 1_123 to the side effect detecting means L_124 according to L types of different calculating methods. Further, the side effect detection result integrating means 125 integrates each side effect detection result, and generates a final side effect detection result.

Meanwhile, a specific example of an operation according to a configuration illustrated in FIG. 3 will be described. For example, the abnormality score integrating means 115 generates an abnormality score vector per generation or sex, and the side effect detection result integrating means 125 integrates the side effect detection results created by the side effect detecting means 1_123 to the side effect detecting means L_124 per generation and sex. Further, the side effect detection result integrating means 125 creates a side effect detection result ranked in order from the side effect detection result which is the most suspected to indicate the highest likelihood. By so doing, when, for example, how a side effect appears is different depending on the generation or the sex, it is possible to predict a side effect detection result which is the most suspected to indicate the side effect per generation or sex.

The output device 105 outputs a side effect detection result 107 created by the side effect detecting means 104 or the extended side effect detecting means 108.

The abnormality score vector generating means 103 (more specifically, the abnormality detecting means 1_111 to the abnormality detecting means M_112 and the abnormality score integrating means 115), and the side effect detecting means 104 are realized by a CPU of a computer which operates according to a program (side effect detecting program). Similarly, the abnormality score vector generating means 103 and the extended side effect detecting means 108 (more specifically, the side effect detecting means 1_123 to the side effect detecting means L_124 and the side effect detection result integrating means 125) are realized by the CPU of the computer which operates according to the program (side effect detection program). For example, the program is stored in a memory unit (not illustrated) of the side effect detecting device 100, and the CPU may read this program and operate as the abnormality score vector generating means 103 and the side effect detecting means 104 or the abnormality score vector generating means 103 and the extended side effect detecting means 108.

Further, the abnormality score vector generating means 103 (more specifically, the abnormality detecting means 1_111 to the abnormality detecting means M_112 and the abnormality score integrating means 115) and the side effect detecting means 104 may be each realized by dedicated hardware. Similarly, the abnormality score vector generating means 103 and the extended side effect detecting means 108 (more specifically, the side effect detecting means 1_123 to the side effect detecting means L_124 and the side effect detection result integrating means 125) may be each realized by dedicated hardware.

Next, an operation of the side effect detecting device according to this exemplary embodiment will be described.

Figure 4:
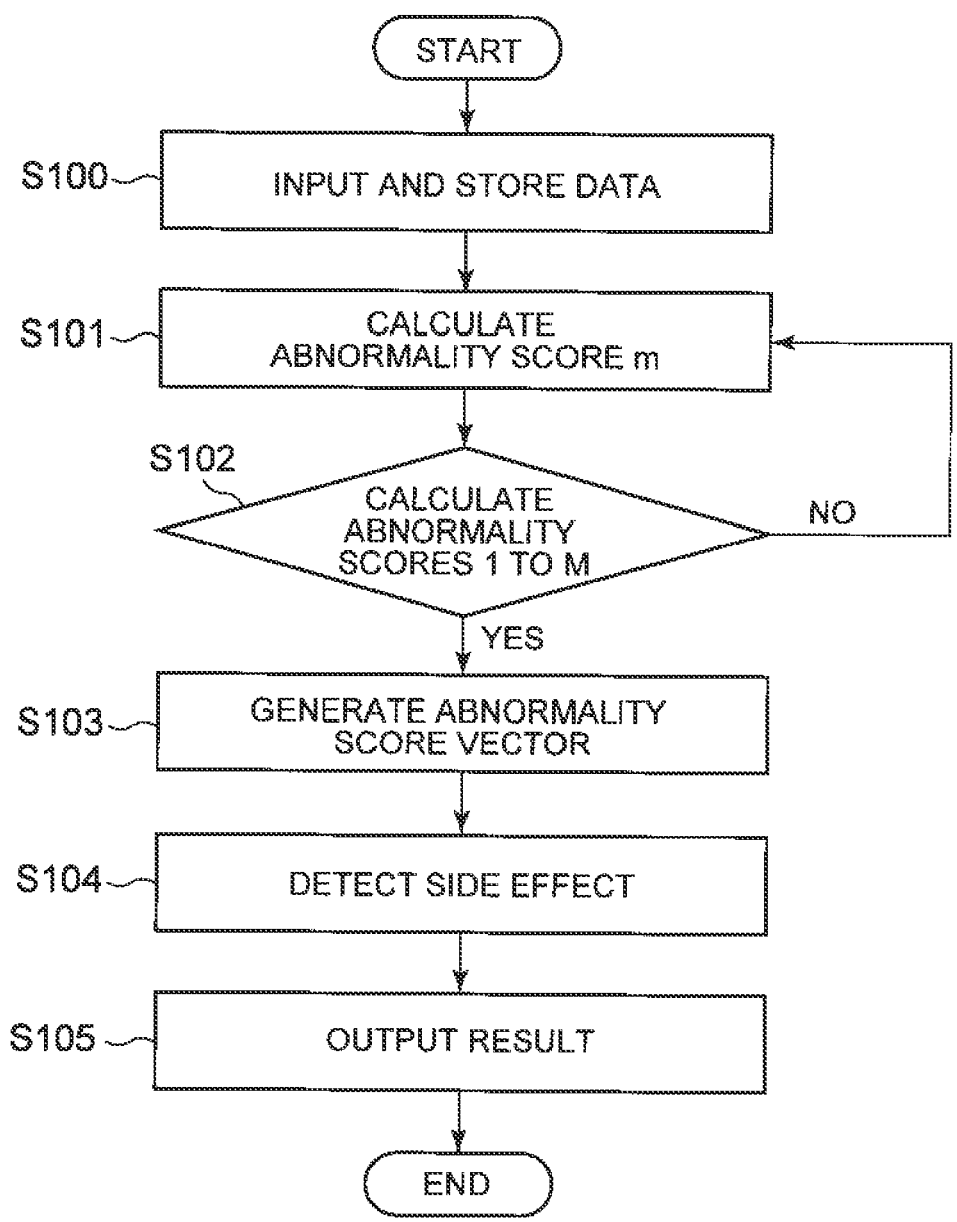
FIG. 4 It depicts a flowchart illustrating an example of an operation of a side effect detecting device 100 which has a side effect detecting means 104.

FIG. 4 is a flowchart illustrating an example of an operation of the side effect detecting device 100 which has the side effect detecting means 104. First, when receiving an input of the input data 106, the input device 101 has the input data memory unit 102 store this data (step S100). Next, each abnormality detecting means calculates an abnormality score based on the input data 106 (step S101). When the abnormality scores 1 to M are not calculated yet (No in step S102), each abnormality detecting means repeats processing of calculating abnormality scores. Meanwhile, when abnormality scores 1 to M are calculated (Yes in step S102), the abnormality score integrating means 115 generates an abnormality score vector based on the calculated abnormality score 1 to the abnormality score M (step S103). Further, the side effect detecting means 104 detects side effects of abnormality score vectors (step S104). Finally, the side effect detecting means 104 has the output device 105 output the side effect detection result (step S105).

Figure 5:
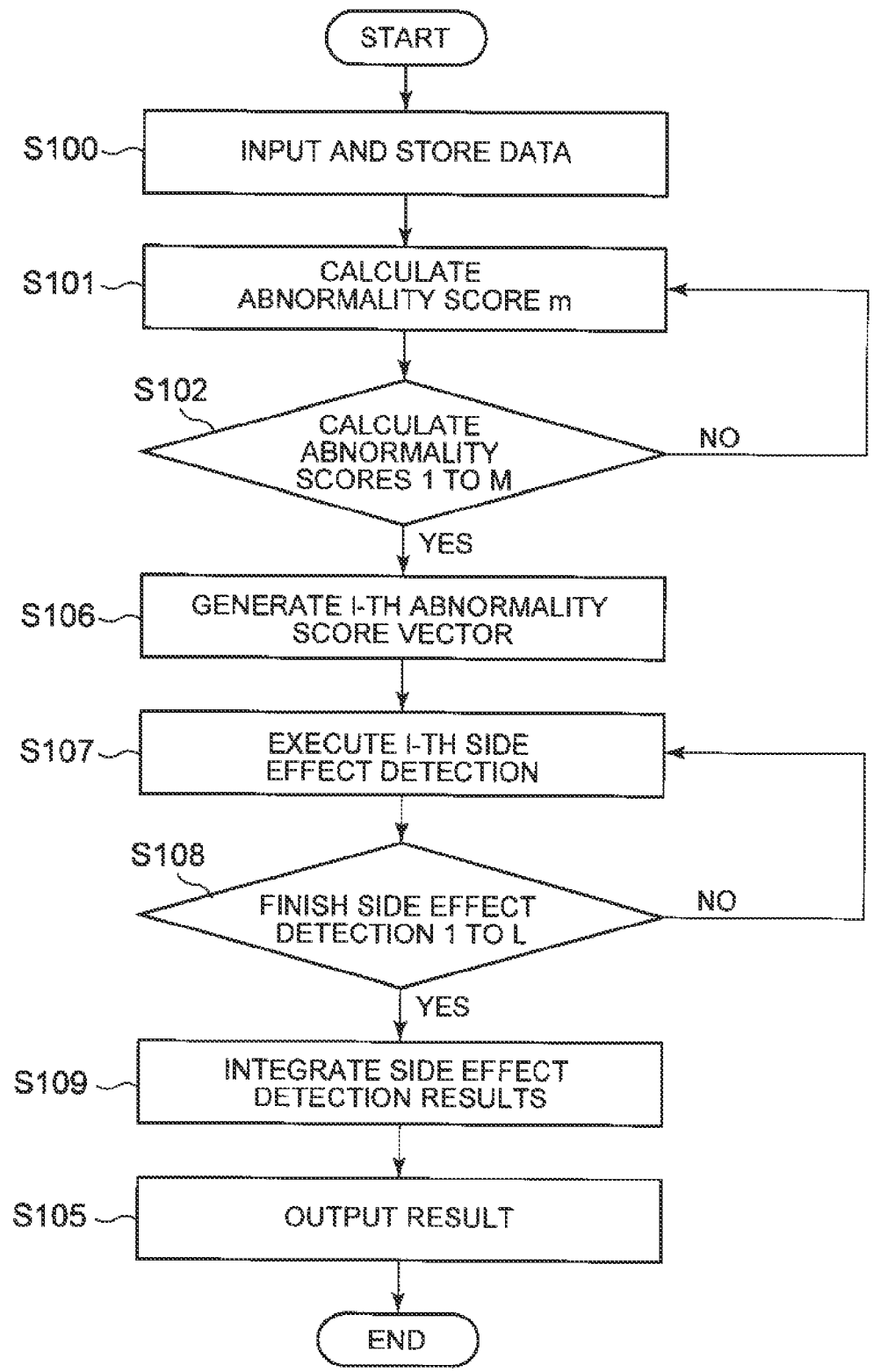
FIG. 5 It depicts a flowchart illustrating an example of an operation of the side effect detecting device 100 which has an extended side effect detecting means 108.

Further, FIG. 5 is a flowchart illustrating an example of the operation of the side effect detecting device 100 which has the extended side effect detecting means 108 illustrated in FIG. 3. Processings in steps S100 to S102 of receiving an input of the input data 106 and calculating the abnormality score in each abnormality detecting means are the same as processing in FIG. 4.

When an abnormality score is calculated, the abnormality score integrating means 115 generates L types of abnormality score vectors (step S106). The extended side effect detecting means 108 (more specifically, each of the side effect detecting means 1_123 to the side effect detecting means L_124) detects the side effect for each abnormality score (step S107). When side effects are not detected for all of the abnormality score vector 1_121 to the abnormality score vector L_122 (No in step S108), the extended side effect detecting means 108 performs processing of detecting side effects in the rest of abnormality score vectors. Meanwhile, when detection of side effects is finished for all of the abnormality score vector 1_121 to the abnormality score vector L_122 (Yes in step S108), the side effect detection result integrating means 125 integrates each side effect detection result (step S109). Further, the side effect detection result integrating means 125 has the output device 105 output a side effect detection result (step S105).

That is, when the side effect detecting device 100 has the extended side effect detecting means 108, a difference from processing in FIG. 4 (that is, the processing performed by the side effect detecting means 104) is that the extended side effect detecting means 108 performs 1st to L-th side effect detections (steps S106 to S108 in FIG. 5) and the side effect detection result integrating means 125 integrates the side effect detection results (step S109 in FIG. 5).

As described above, according to this exemplary embodiment, the abnormality detecting means calculates the abnormality score of each data xn based on specificity of each data. Further, the abnormality score integrating means 115 integrates the abnormality scores to create the abnormality score vector. Subsequently, the side effect detecting means 104 decides the likelihood of the side effect indicated by the abnormality score vector according to a predetermined rule (for example, a weighted sum of abnormality scores, a classification model or a regression model). Further, the side effect detecting means 104 detects an abnormality score vector the likelihood of which satisfies conditions set in advance (for example, a predetermined threshold or a learning result of the classification model or the regression model) as information indicating a side effect (for example, extract a target abnormality score vector or present in a ranking format).

According to this configuration, it is possible to extract an unknown side effect of a drug from information related to medical treatment. Consequently, it is possible to quickly detect a side effect of a drug which could occur in the market.

More specifically, by representing data of medical information using abnormality scores, it is possible to detect a side effect based on the property of data which is common between various side effects (for example, a rapid change in the amount of prescription when a side effect occurs or a rapid increase in a medical expense). That is, each information is characterized by using an abnormality score and a side effect is detected based on these pieces of information, so that it is possible to detect not only known side effects recorded in the side effect DB but also side effects which are not recorded, so that it is possible to detect unknown side effects which cannot be detected based only on epidemiological opinions, for example, "what kind of side effect occurs from a given group of drugs".

Further, even though occurrence of a disease is disclosed in chart information, receipt information, health diagnosis information or diagnosis group classification (DPC), whether the disease is a side effect is not usually disclosed. Hence, a general side effect detecting technique has difficulty in making the most of these pieces of information utilized for detecting a side effect. However, according to this exemplary embodiment, it is possible to utilize not only information in the side effect DB but also various pieces of medical information such as charts and receipts and, consequently, quickly discover a side effect which is occurring in the market.

Second Exemplary Embodiment

Figure 6:
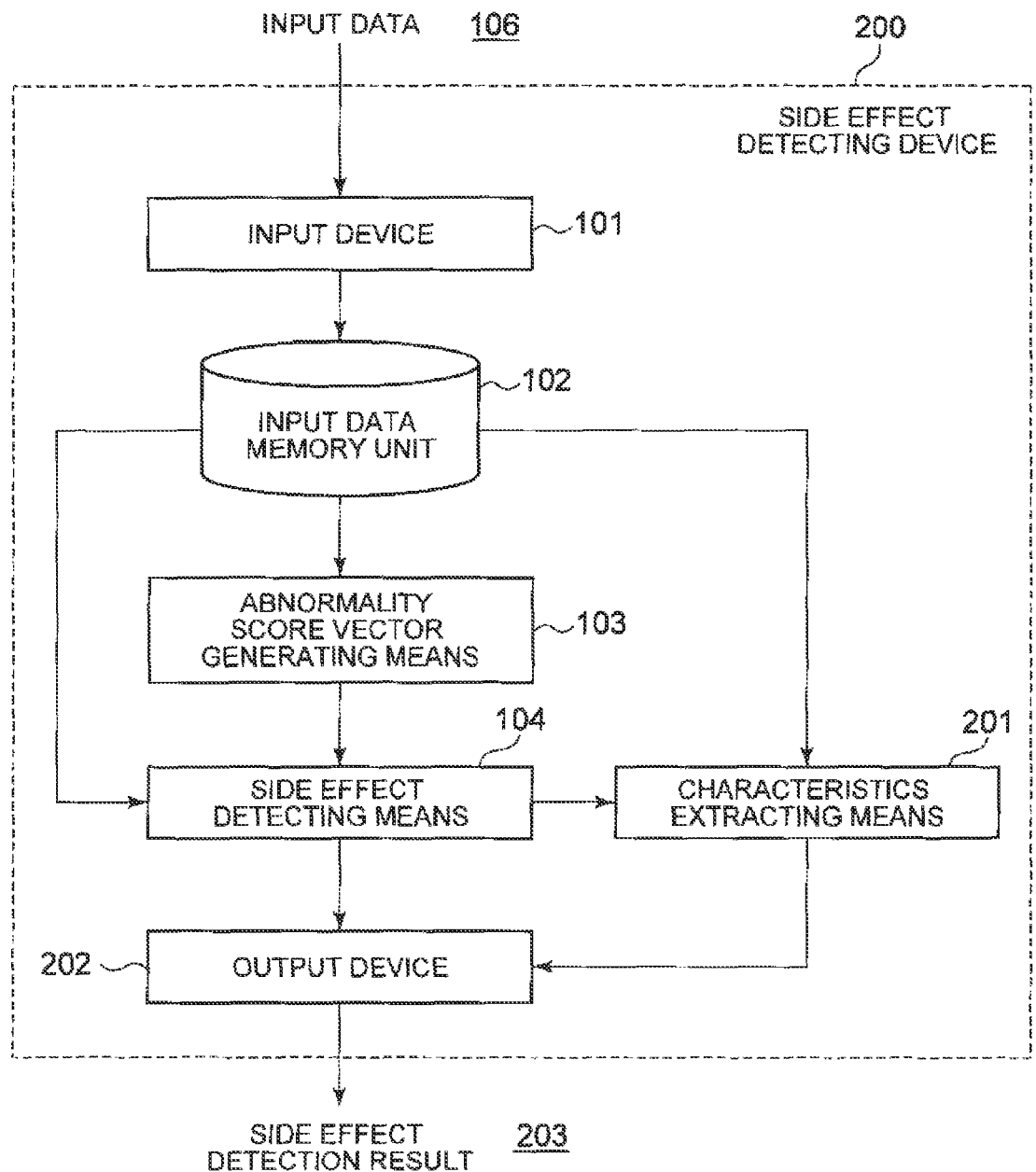
FIG. 6 It depicts a block diagram illustrating an example of a side effect detecting device according to a second exemplary embodiment of this invention.

FIG. 6 is a block diagram illustrating an example of a device (side effect detecting device) which extracts an abnormality event from medical information according to a second exemplary embodiment of this invention. In addition, the same configurations as in the first exemplary embodiment will be assigned the same reference numerals as in FIG. 1, and will not be described. A side effect detecting device 200 according to this exemplary embodiment has an input device 101, an input data memory unit 102, an abnormality score vector generating means 103, a side effect detecting means 104, a characteristics extracting means 201 and an output device 202. The input device 101 receives an input of input data 106. Further, the output device 202 outputs a side effect detection result 203.

That is, the side effect detecting device 200 according to this exemplary embodiment differs from a side effect detecting device 100 according to the first exemplary embodiment in including the characteristics extracting means 201. Further, the first exemplary embodiment differs from this exemplary embodiment in that the output device 105 and a side effect detection result 107 of the side effect detecting device 100 according to the first exemplary embodiment are replaced with the output device 202 and a side effect detection result 203 of the side effect detecting device 200 according to this exemplary embodiment. The other configurations are the same as in the first exemplary embodiment.

The output device 202 has a function of the output device 105 according to the first exemplary embodiment and, in addition, a function of outputting a result extracted by the characteristics extracting means 201 described below. Further, the side effect detection result 203 includes content of the side effect detection result 107 according to the first exemplary embodiment and, in addition, a result extracted by the characteristics extracting means 201.

The characteristics extracting means 201 extracts a characteristics of the side effect detection result according to an arbitrary method based on the side effect detection result detected by the side effect detecting means 104 or input data read from the input data memory unit 102. That is, the characteristics extracting means 201 extracts a characteristic element from the abnormality score vector detected as information indicating a side effect or from input data specified based on this abnormality score vector.

A specific example of extracting a characteristic element is a method of extracting a characteristic element of an abnormality score vector which is suspected to indicate a side effect or input data linked to the abnormality score vector. A method of utilizing main component analysis will be described as an example of a method of extracting a characteristic element. The characteristics extracting means 201 applies main component analysis to an abnormality score vector which is suspected to indicate a side effect as a side effect detection result, and extracts an element of a higher main component score as a characteristic element. Meanwhile, an abnormality score vector which is suspected to indicate a side effect includes an abnormality score vector which is decided to be a side effect or an abnormality score vector of a side effect detection result of a higher ranking.

In addition, a method of extracting a characteristic element in the characteristics extracting means 201 is not limited to the above method. The characteristics extracting means 201 may extract as a characteristic element, for example, an element having a difference between an abnormality score vector which is suspected to indicate a side effect and an abnormality score vector which has a low likelihood of a side effect, and an element having a characteristic difference between input data connected to these abnormality score vectors. A specific method of extracting an element having a characteristic difference is a method of analyzing main components of data which is suspected to indicate a side effect and data which has a low likelihood of a side effect, extracting a characteristic element of a high main component score and extracting an element which is not common between both items of data.

In addition, the characteristics extracting means 201 may decide and analyze data which is suspected to indicate a side effect and data which has a low likelihood of a side effect and extract an element of a high absolute value of a projection vector to extract a characteristic element.

The abnormality score vector generating means 103, the side effect detecting means 104 and the characteristics extracting means 201 are realized by the CPU of the computer which operates according to the program (side effect detecting program). Further, the abnormality score vector generating means 103, the side effect detecting means 104 and the characteristics extracting means 201 may be each realized by dedicated hardware.

Figure 7:
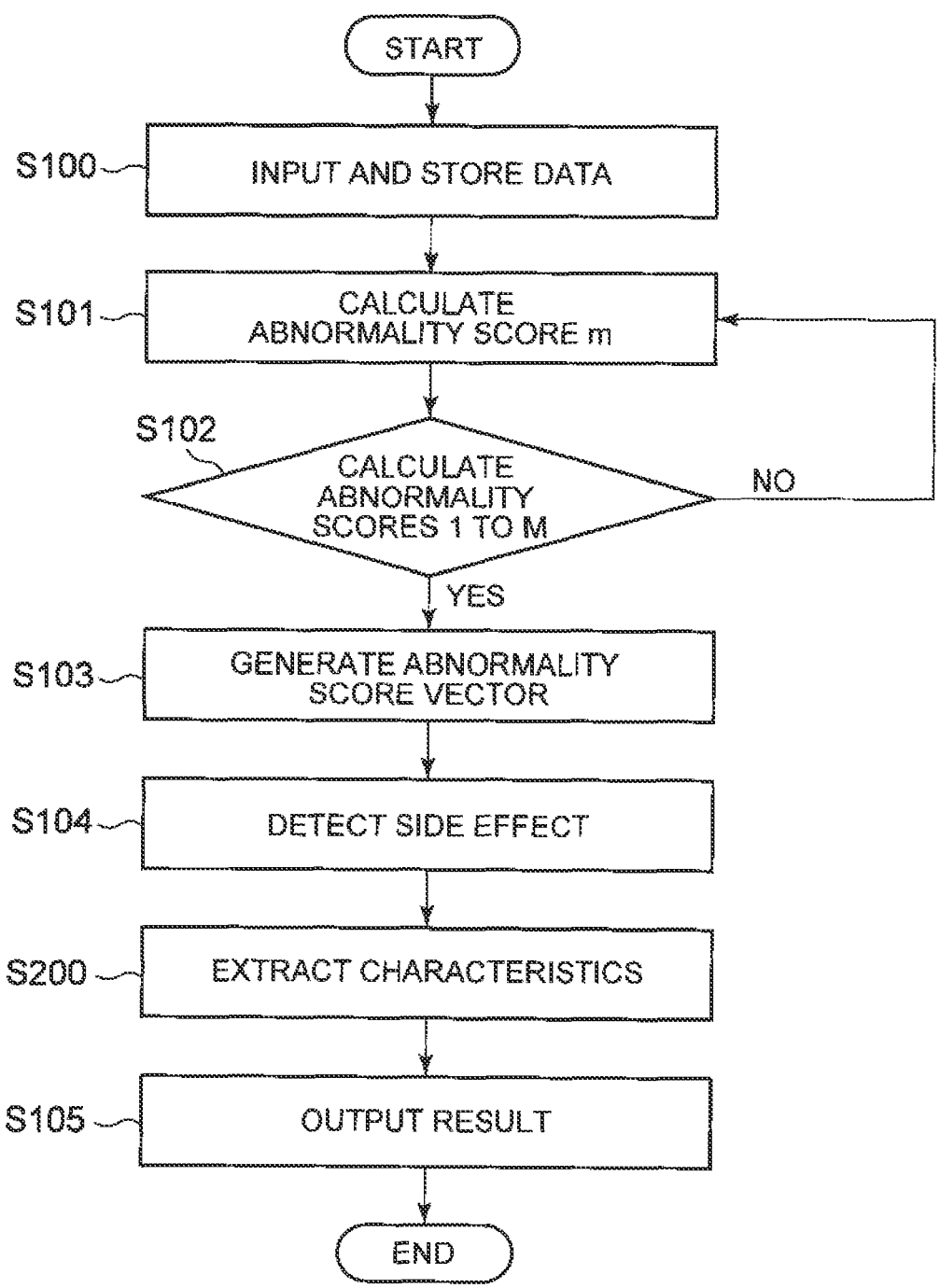
FIG. 7 It depicts a flowchart illustrating an example of an operation of a side effect detecting device 200 according to the second exemplary embodiment.

Next, an operation of the side effect detecting device according to this exemplary embodiment will be described. FIG. 7 illustrates a flowchart illustrating an example of an operation of the side effect detecting device 200 according to the second exemplary embodiment. Processings in steps S100 to S104 of receiving an input of the input data 106 and detecting a side effect are the same as processings in steps S100 to S104 in FIG. 4.

When the side effect detecting means 104 detects a side effect, the characteristics extracting means 201 extracts characteristics from a side effect detection result or the input data 106 (step S200). Further, the characteristics extracting means 201 has the output device 202 output the side effect detection result and the characteristics extraction result (step S105). As described above, the operation of the side effect detecting device 200 differs from the operation of the side effect detecting device 100 only in including processing of extracting characteristics (step S200 in FIG. 7).

As described above, with this exemplary embodiment, the characteristics extracting means 201 extracts a characteristic element from the abnormality score vector detected as information indicating a side effect or from the input data 106 specified by this abnormality score vector. More specifically, with this exemplary embodiment, not only data which is suspected to indicate a side effect or an abnormality score vector in this case but also a characteristic point of this data is extracted. Consequently, it is possible to provide information which is useful for users to finally analyze a side effect. This is particularly highly effective because users cannot learn the characteristics in advance when an unknown side effect is intended to be detected.

Third Exemplary Embodiment

Figure 8:
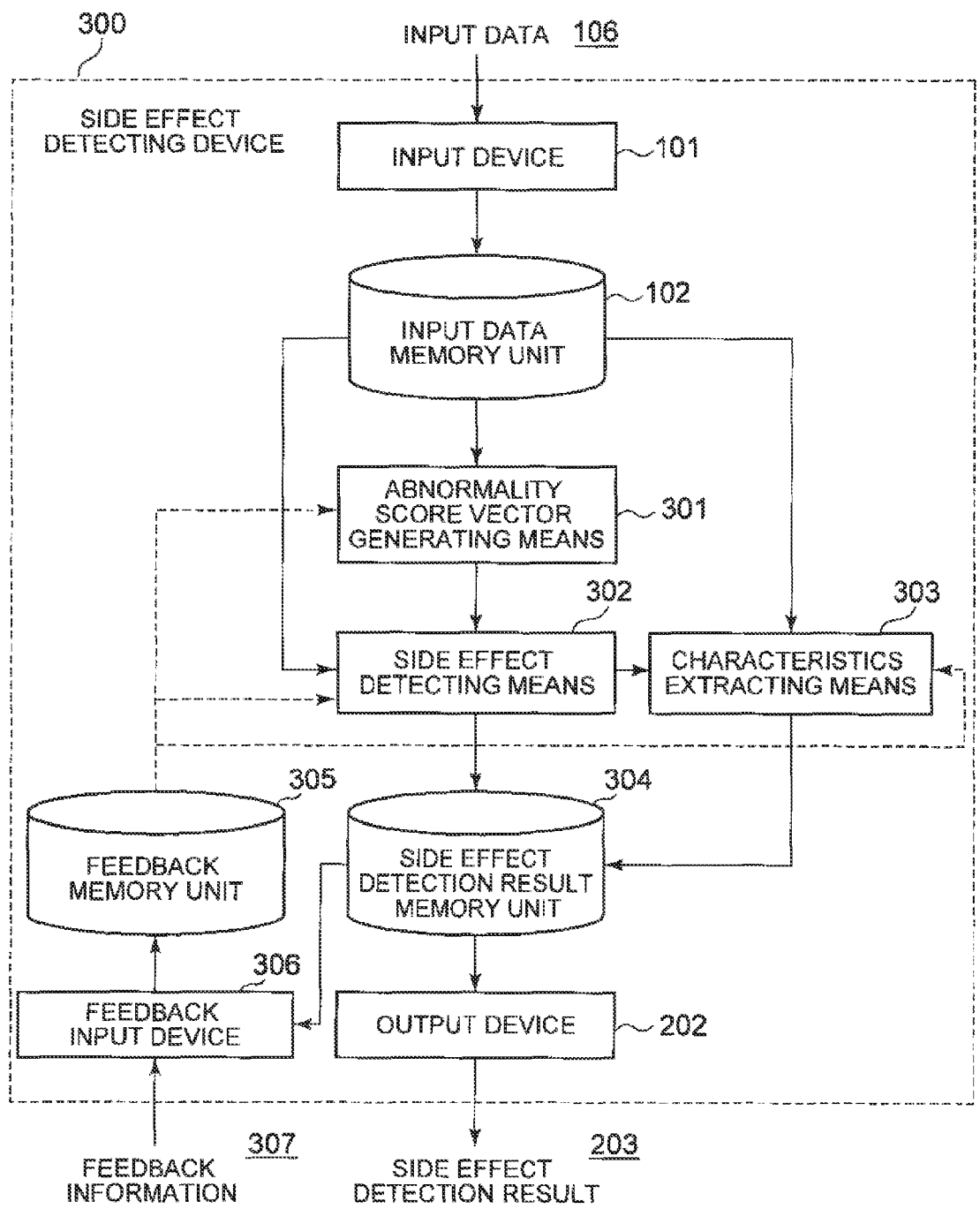
FIG. 8 It depicts a block diagram illustrating an example of a side effect detecting device according to a third exemplary embodiment of this invention.

FIG. 8 is a block diagram illustrating an example of a device (side effect detecting device) which extracts an abnormality event from medical information according to a third exemplary embodiment of this invention. In addition, the same configurations as in the second exemplary embodiment will be assigned the same reference numerals as in FIG. 1, and will not be described. A side effect detecting device 300 according to this exemplary embodiment has an input device 101, an input data memory unit 102, an abnormality score vector generating means 301, an extended side effect detecting means 302, an extended characteristics extracting means 303, a side effect detection result memory unit 304, a feedback memory unit 305, a feedback input device 306 and an output device 202. The input device 101 receives an input of input data 106. Further, the output device 202 outputs a side effect detection result 203. Furthermore, the feedback input device 306 receives an input of feedback information 307.

That is, the side effect detecting device 300 according to this exemplary embodiment differs from a side effect detecting device 200 according to the second exemplary embodiment in including the side effect detection result memory unit 304, the feedback memory unit 305 and the feedback input device 306. Further, the second exemplary embodiment differs from this exemplary embodiment in that an abnormality score vector generating means 103, the side effect detecting means 104 and the characteristics extracting means 201 according to the second exemplary embodiment are replaced with the abnormality score vector generating means 301, the extended side effect detecting means 302 and the extended characteristics extracting means 303 of the side effect detecting device 300 according to this exemplary embodiment. Furthermore, the side effect detecting device 300 according to the third exemplary embodiment differs from the side effect detecting device 200 according to the second exemplary embodiment in that the feedback input device 306 receives an input of the feedback information 307. The configurations other than that are the same as in the second exemplary embodiment.

The feedback information 307 is information used to analyze a side effect, and includes arbitrary information such as information based on users' knowledge or empirical rules, information indicating a view point of analyzing a side effect, a processing method of calculating an abnormality score and a processing method of extracting a characteristic element from the input information. Further, the information included in the feedback information 307 may include processing of using this information or information for identifying means which performs this processing. More specifically, the feedback information 307 is used in each processing performed by the abnormality score vector generating means 301, the extended side effect detecting means 302 and the extended characteristics extracting means 303. Hence, a specific example of the feedback information 307 will be described upon description of the abnormality score vector generating means 301, the extended side effect detecting means 302 and the extended characteristics extracting means 303 described below.

The feedback input device 306 is a device for receiving an input of the feedback information 307. More specifically, for example, the feedback input device 306 has the feedback memory unit 305 store the feedback information 307 input by a user. Further, the feedback input device 306 has the feedback memory unit 305 also store analysis information stored in the side effect detection result memory unit 304 described below as feedback information.

The feedback memory unit 305 stores the feedback information 307. The feedback memory unit 305 is realized by, for example, a magnetic disk.

The side effect detection result memory unit 304 stores results of side effects detected by the extended side effect detecting means 302 and characteristic elements extracted by the extended characteristics extracting means 303. In addition, these pieces of information stored in the side effect detection result memory unit 304 are received as input by the feedback input device 306 as feedback information.

Figure 9:
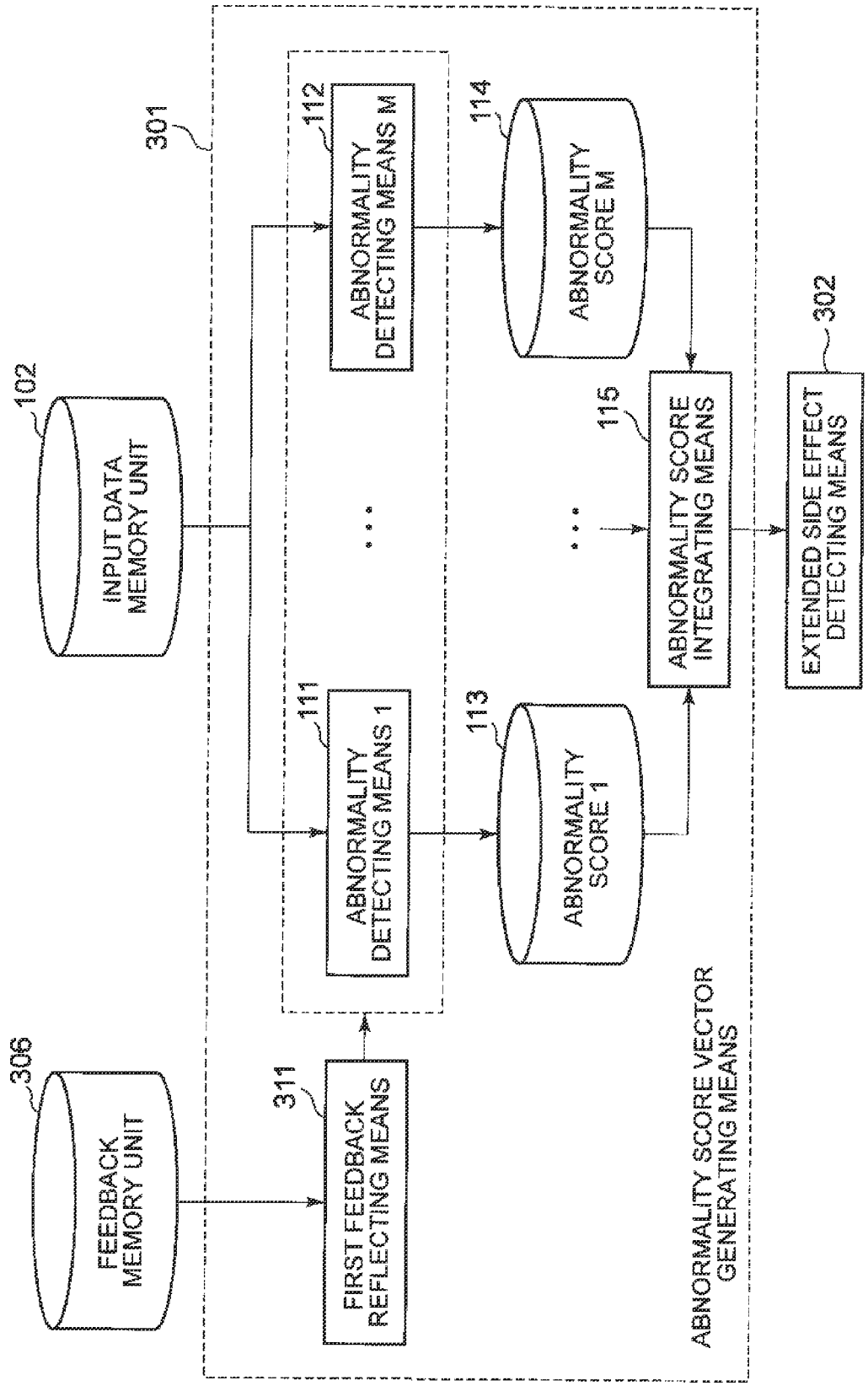
FIG. 9 It depicts an explanatory view illustrating an example of an abnormality score vector generating means 301.

FIG. 9 is an explanatory view illustrating an example of the abnormality score vector generating means 301 according to this exemplary embodiment. The abnormality score vector generating means 301 has a first feedback reflecting means 311, an abnormality detecting means 1_111 to an abnormality detecting means M_112 (that is, "abnormality detecting means") and an abnormality score integrating means 115. That is, the abnormality score vector generating means 301 according to this exemplary embodiment differs from the abnormality score vector generating means 103 according to the first exemplary embodiment in including the first feedback reflecting means 311.

Further, the abnormality score vector generating means 301 differs from the first exemplary embodiment in instructing calculation of abnormality scores using both of information stored in the input data memory unit 102 and information stored in the feedback memory unit 305. Furthermore, the first feedback reflecting means 311 differs from the first exemplary embodiment in reading the feedback information from the feedback memory unit 305 and reflecting this information by using an arbitrary method in each abnormality detecting means and the abnormality score integrating means 115. Hereinafter, processing of the first feedback reflecting means 311 will be described.

The first feedback reflecting means 311 controls the operation of the abnormality detecting means based on the feedback information 307. More specifically, when information used to create an abnormality score (for example, information which has been already analyzed or a processing method of calculating an abnormality score) is input as the feedback information 307, the first feedback reflecting means 311 has the abnormality detecting means create an abnormality score based on this information. In addition, controlling the operation of the abnormality detecting means based on the feedback information 307 by means of the first feedback reflecting means 311 is described as reflecting feedback information by means of the first feedback reflecting means 311.

A method of reflecting feedback information by means of the first feedback reflecting means 311 includes, for example, adding a new abnormality detecting means or removing an abnormality detecting means which is currently utilized. Meanwhile, adding a new abnormality detecting means means adding new processing of detecting an abnormality score. Further, removing an abnormality detecting means which is currently utilized means stops performing part of abnormality score detection processing which has been performed so far. When an abnormality detecting means is added or removed as feedback reflecting processing, the number and the type of abnormality detecting means to be utilized are changed before and after the feedback is reflected (that is, processing of detecting abnormality scores is changed), and an abnormality score vector which is finally generated is also changed.

Meanwhile, an example of an operation of the first feedback reflecting means 311 of adding abnormality detecting means will be described. For example, information of (1) ["definition of a new abnormality detecting means and "addition"] is input to the feedback input device 306 as the feedback information 307 according to, for example, a user's instruction, and is stored in the feedback memory unit 305. Next, when the feedback information 307 of (2) ["reflection of feedback"] is input at the same time as an addition timing or at another timing, this input triggers the first feedback reflecting means 311 to decide to add an abnormality detecting means. A decision method upon removal is also the same as the above method. In addition, in case of this example, when the information indicated by (1) is input as the feedback information 307 and the information indicated by (2) is not input, only the information indicated by (1) is accumulated. Further, at a timing when the information indicated by (2) is inputted, a plurality of pieces of information indicated by (1) is reflected at a time. Meanwhile, information to be reflected may be selected at a timing when the information indicated by (2) is input.

In addition, the first feedback reflecting means 311 may instruct each abnormality detecting means to calculate an abnormality score using both of information stored in the input data memory unit 102 and the information stored in the feedback memory unit 305. More specifically, for example, feedback information that "a risk of a side effect is high when two given drugs are taken at the same time" is input. In this case, the first feedback reflecting means 311 may instruct each abnormality detecting means to correct an abnormality score vector of corresponding data to a high abnormality score vector. By performing processing of reflecting this feedback information in the abnormality score vector generating means 301 (more specifically, each abnormality detecting means), the first feedback reflecting means 311 can define a new abnormality score vector without adding a new abnormality detecting means.

Another example of a method of reflecting the feedback information by means of the first feedback reflecting means 311 includes assigning information whether or not a side effect occurs or seriousness information as feedback information for data decided to be suspected to indicate a side effect by the side effect detection result 203. By reflecting such information in the abnormality detecting means which utilizes whether or not a side effect occurs or seriousness information, it is possible to improve precision to detect abnormality.

Further, the first feedback reflecting means 311 may refer to a side effect detection result, and assigns information whether or not a side effect occurs or seriousness information to an abnormality score vector. More specifically, the first feedback reflecting means 311 may associate new side effect/seriousness information yn with data xn linked to an abnormality score vector wi.

As described above, the first feedback reflecting means 311 reflects feedback information in processing of generating an abnormality score vector, so that it is possible to provide various effects. For example, it is possible to perform processing of detecting a side effect from a new view point (that is, detection of a new side effect), reduce an error detection rate of a side effect and perform processing of detecting a side effect by aiming at a target (for example, configure an abnormality score vector which is effective only for a specific drug class).

Figure 10:
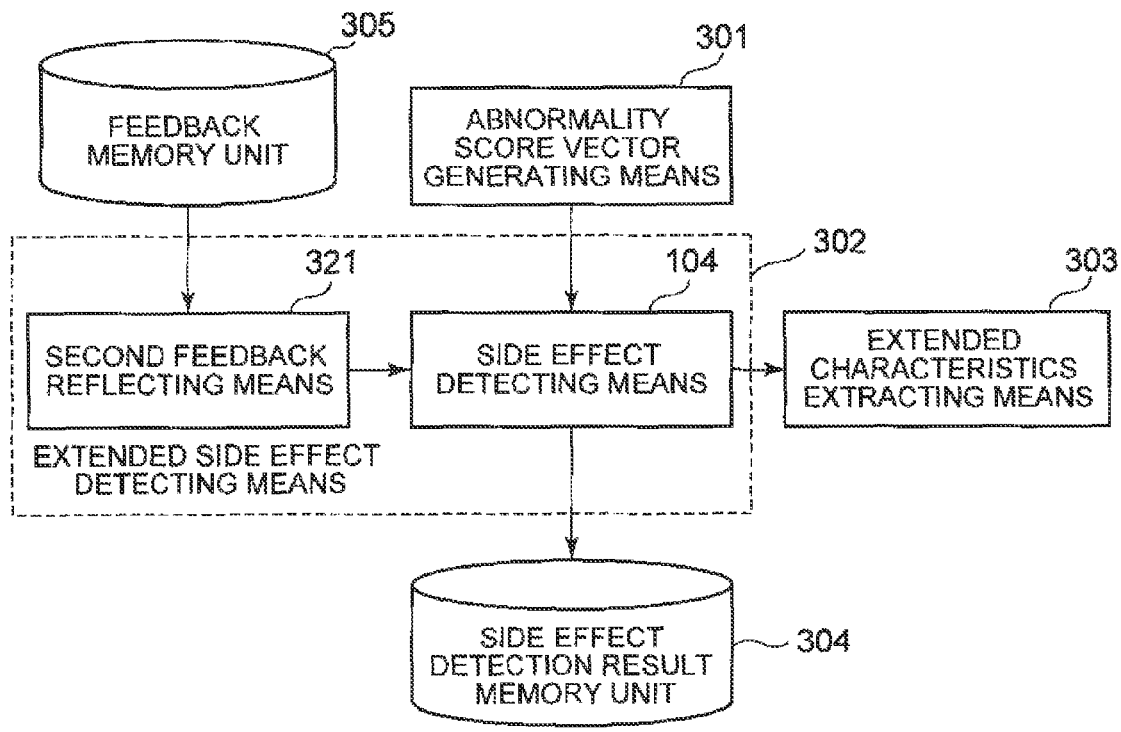
FIG. 10 It depicts an explanatory view illustrating an example of an extended side effect detecting means 302.

FIG. 10 is an explanatory view illustrating an example of the extended side effect detecting means 302 according to the present exemplary embodiment. The extended side effect detecting means 302 includes a second feedback reflecting means 321 and a side effect detecting means 104. The side effect detecting means 302 according to the present exemplary embodiment differs from the side effect detecting means 104 according to the first exemplary embodiment in including the second feedback reflecting means 321. Further, the second feedback reflecting means 321 differs from the first exemplary embodiment in reading feedback information from the feedback memory unit 305, and reflecting this information in the side effect detecting means 104 by using an arbitrary method. Hereinafter, processing of the second feedback reflecting means 321 will be described.

The second feedback reflecting means 321 controls the operation of the side effect detecting means 104 based on the feedback information 307. More specifically, when information used to detect a side effect (for example, information which has been already analyzed or information indicating a view point of detecting a side effect) is input as the feedback information 307, the second feedback reflecting means 321 has the extended side effect detecting means 302 detect a side effect based on this information. In addition, in some cases, controlling the operation of the side effect detecting means 104 based on the feedback information 307 by means of the second feedback reflecting means 321 is described as reflecting feedback information by means of the second feedback reflecting means 321.

Another example of a method of reflecting the feedback information by means of the second feedback reflecting means 321 includes providing information whether or not a side effect occurs or seriousness information as feedback information in data decided to be suspected to indicate a side effect (high likelihood) by the side effect detection result 203. In addition, when the side effect detecting means 104 learns a classification model of an abnormality score vector linked to data indicating the side effect, and an abnormality score vector linked to data without the side effect, the number of items of learning target "data having a likelihood of a side effect" increases. Consequently, it is possible to improve precision of a classification model. Further, the second feedback reflecting means 321 may label data on which whether or not a side effect occurs is decided. In addition, part of data may be a labeling target. By assigning such a label, whether or not a side effect occurs in each data becomes clear, so that it is possible to improve precision of a classification model.

A case has been described where the side effect detecting means 104 learns a classification model. In addition, the same applies to other models such as a regression model and a ranking model which the side effect detecting means 104 learns utilizing a side effect label or seriousness. Thus, by utilizing analyzed information to detect a side effect (for example, utilizing as learning data for a side effect detection model or utilizing for correction of a ranking of side effect detection results), it is possible to improve precision to detect a side effect.

Further, the side effect detecting means 104 has the side effect detection result memory unit 304 store a side effect detection result.

Figure 11:
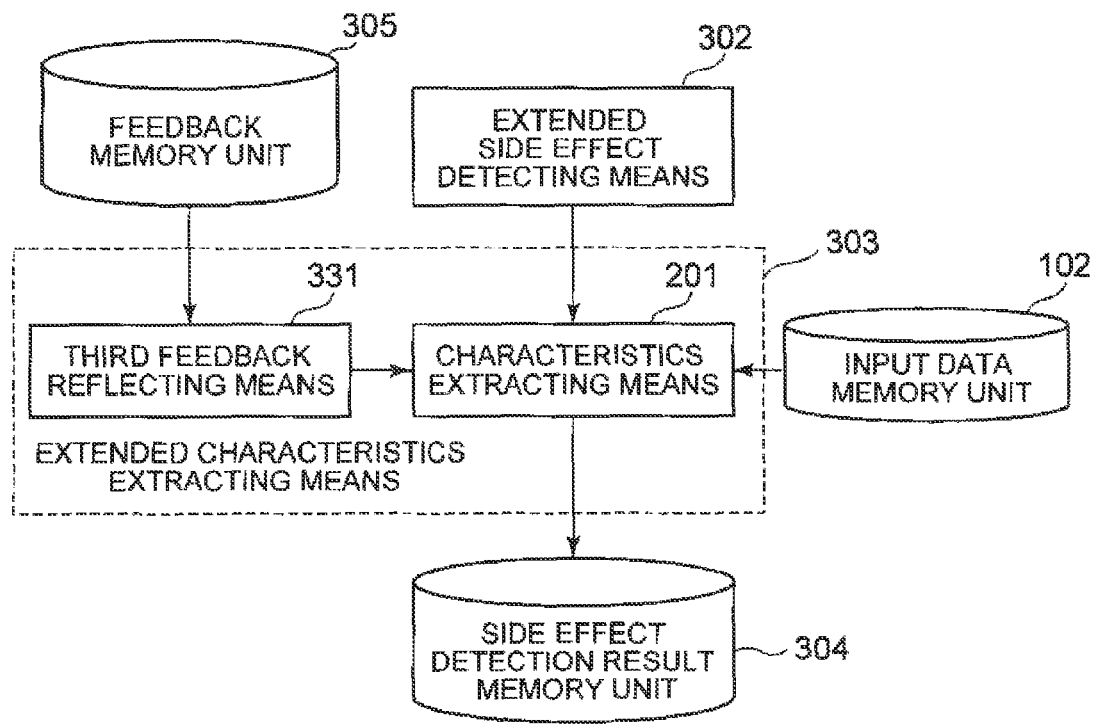
FIG. 11 It depicts an explanatory view illustrating an example of extended characteristics extracting means 303.

FIG. 11 is an explanatory view illustrating an example of the extended characteristics extracting means 303 according to this exemplary embodiment. The extended characteristics extracting means 303 include a third feedback reflecting means 331 and a characteristics extracting means 201. The extended characteristics extracting means 303 according to this exemplary embodiment differs from a characteristics extracting means 201 according to the second exemplary embodiment in including the third feedback reflecting means 331. Further, the third feedback reflecting means 331 differs from the second exemplary embodiment in reading feedback information from the feedback memory unit 305, and reflecting this information in the characteristics extracting means 201 by using an arbitrary method. Hereinafter, processing of the third feedback reflecting means 331 will be described.

The third feedback reflecting means 331 controls the operation of the extended characteristics extracting means 303 based on the feedback information 307. More specifically, when information which is used to extract a characteristic element from input data or a side effect detection result (for example, information which has already been analyzed or a processing method of extracting a characteristic element from input information) is input as the feedback information 307, the third feedback reflecting means 331 has the extended characteristics extracting means 303 extract the characteristic element from the above information based on this information. In addition, in some cases, controlling the operation of the extended characteristics extracting means 303 based on the feedback information 307 by means of the third feedback reflecting means 331 is described as reflecting feedback information by means of the third feedback reflecting means 331.

An example of a method of reflecting feedback information by means of the third feedback reflecting means 331 includes addition of a new characteristics extracting means or removal of a characteristics extracting means which is currently utilized. Meanwhile, addition of a new characteristics extracting means adding new processing of extracting a characteristic element. Further, removing a characteristics extracting means which is currently utilized means skipping part of characteristic element extraction processing which has been performed so far. In addition, a method of adding a new characteristics extracting means or removing a characteristics extracting means which is currently utilized by means of the third feedback reflecting means 331 is the same method of adding a new abnormality detecting means or removing an abnormality detecting means which is currently utilized by means of the first feedback reflecting means 311. When, for example, a new processing method of extracting a characteristic element is input as feedback information, the third feedback reflecting means 331 may add a new characteristics extracting means.

Further, as feedback information, the third feedback reflecting means 331 gives information such as whether or not a side effect occurs or seriousness information (for example, information indicating which an abnormality score or side effect detection result is important or unimportant, or contraindication information) to the characteristics extracting means 201. By giving this information, even when, for example, whether or not a side effect occurs or seriousness information is not included in the original input data, the characteristics extracting means 201 can extract (for example, decide and analyze) characteristics based on whether or not a side effect occurs or seriousness information.

Further, when, for example, the characteristics extracting means 201 performs processing of extracting as characteristics a difference between data which is suspected to indicate a side effect and data which has a low likelihood of a side effect, giving information whether or not a side effect occurs or seriousness information to the characteristics extracting means 201 as feedback information is effective. By giving information whether or not a side effect occurs or seriousness information to the characteristics extracting means 201 as feedback information, the characteristics extracting means 201 can extract characteristics by putting importance on data which is suspected to indicate a side effect and indicates that a side effect occurs and data which has a low likelihood of a side effect and indicates that a side effect does not occur.

Further, the characteristics extracting means 201 has the side effect detection result memory unit 304 store information indicating the extracted characteristics.

In addition, a case has been described above where the abnormality score vector generating means 103 according to the second exemplary embodiment is replaced with the abnormality score vector generating means 301, the side effect detecting means 104 is replaced with the side effect detecting means 302 and the characteristics extracting means 201 is replaced with the extended characteristics extracting means 303. Meanwhile, the side effect detecting device 300 according to this exemplary embodiment may employ a configuration in which at least part of the components above are replaced. In this case, each replaced means (more specifically, the abnormality score vector generating means 301, the extended side effect detecting means 302 and the extended characteristics extracting means 303) may perform processing described in this exemplary embodiment using feedback information.

Further, although this exemplary embodiment has been described upon comparison with the second exemplary embodiment, feedback processing may be performed with respect to the side effect detecting device 100 according to the first exemplary embodiment. More specifically, it is only necessary to replace the abnormality score vector generating means 103 with the abnormality score vector generating means 301, and the side effect detecting means 104 with the extended side effect detecting means 302.

The abnormality score vector generating means 301 (more specifically, the first feedback reflecting means 311, the abnormality detecting means 1_111 to the abnormality detecting means M_112 (that is, the abnormality detecting means) and the abnormality score integrating means 115), the extended side effect detecting means 302 (more specifically, the second feedback reflecting means 321 and the side effect detecting means 104), and the extended characteristics extracting means 303 (more specifically, the third feedback reflecting means 331 and the characteristics extracting means 201) are realized by a CPU of a computer which operates according to a program (side effect detecting program). Further, the abnormality score vector generating means 301, the extended side effect detecting means 302 and the extended characteristics extracting means 303 may be each realized by dedicated hardware.

Figure 12:
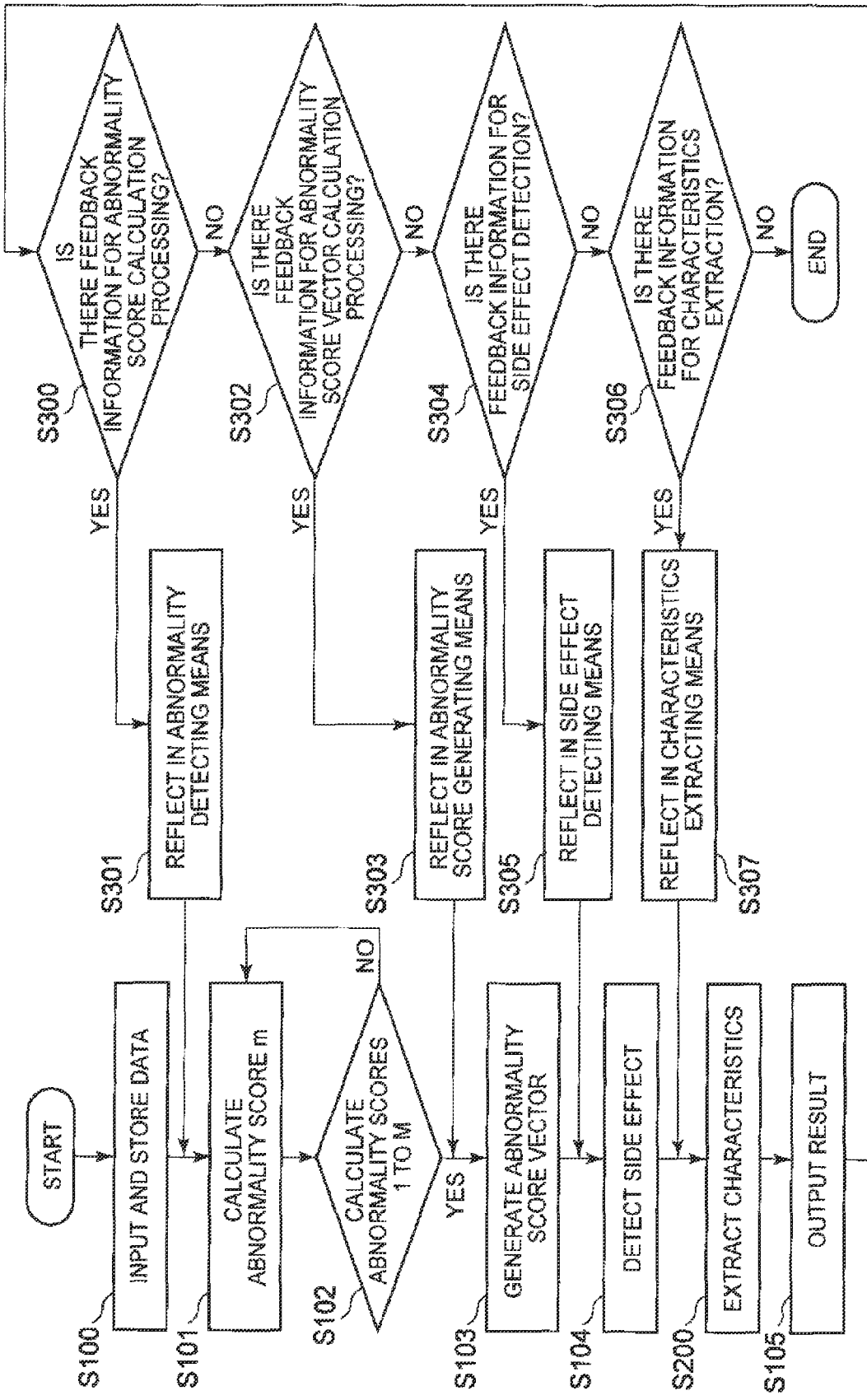
FIG. 12 It depicts a flowchart illustrating an example of an operation of a side effect detecting device 300 according to the third exemplary embodiment.

Next, an operation of the side effect detecting device according to this exemplary embodiment will be described. FIG. 12 is a flowchart illustrating an example of an operation of the side effect detecting device 300 according to the third exemplary embodiment. The operation of the side effect detecting device 300 according to this exemplary embodiment differs from the operation of the side effect detecting device 200 according to the second exemplary embodiment in including feedback processing. That is, processings in steps S100 to S105 of receiving an input of the input data 106 and detecting a side effect are the same as processings in steps S100 to S105 in FIG. 7.

When a side effect detection result and a characteristics extraction result are stored in the side effect detection result memory unit 304, the first feedback reflecting means 311 decides whether or not feedback information for abnormality score calculation processing is stored in the feedback memory unit 305 (step S300). When there is feedback information for the abnormality score calculation processing (Yes in step S300), the first feedback reflecting means 311 reflects the feedback information in the abnormality detecting means (step S301), and performs processing subsequent to step S101.

When there is not feedback information for the abnormality score calculation processing (No in step S300), the first feedback reflecting means 311 decides whether or not the feedback information for the abnormality score vector calculation processing is stored in the feedback memory unit 305 (step S302). When there is feedback information for the abnormality score vector calculation processing (Yes in step S302), the first feedback reflecting means 311 reflects the feedback information in the abnormality score integrating means 115 (step S303), and performs processing subsequent to step S103.

When there is not feedback information for the abnormality score vector calculation processing (No in step S302), the second feedback reflecting means 321 decides whether or not the feedback information for side effect detection is stored in the feedback memory unit 305 (step S304). When there is feedback information for side effect detection (Yes in step S304), the second feedback reflecting means 321 reflects the feedback information in the side effect detecting means 104 (step S305), and performs processing subsequent to step S104.

When there is not feedback information for side effect detection (No in step S304), the third feedback reflecting means 331 decides whether or not the feedback information for characteristic extraction is stored in the feedback memory unit 305 (step S306). When there is feedback information for characteristic extraction (Yes in step S306), the third feedback reflecting means 331 reflects the feedback information in the characteristics extracting means 201 (step S307), and performs processing subsequent to step S200.

Meanwhile, when there is not feedback information for characteristic extraction (No in step S306), processing is finished without reflecting the feedback information.

As described above, according to this exemplary embodiment, when the feedback input device 306 receives an input of the feedback information 307, if information used by each means to perform processing is input as feedback information, the abnormality detecting means, the extended side effect detecting means 302, and the extended characteristics extracting means 303 perform each processing based on this information. More specifically, when receiving an input of information used to calculate an abnormality score as feedback information, the abnormality detecting means creates an abnormality score based on this information. When receiving an input of information used to create an abnormality score vector as feedback information, the abnormality score integrating means 115 creates the abnormality score vector based on this information. When receiving an input of information used to detect a side effect as feedback information, the extended side effect detecting means 302 detects the side effect based on this information. When receiving an input of information used to extract characteristics as feedback information, the extended characteristics extracting means 303 extracts characteristics based on this information. Thus, by using feedback information, it is possible to make an operation of extracting a side effect from a great amount of accumulated information efficient.

Figure 13:
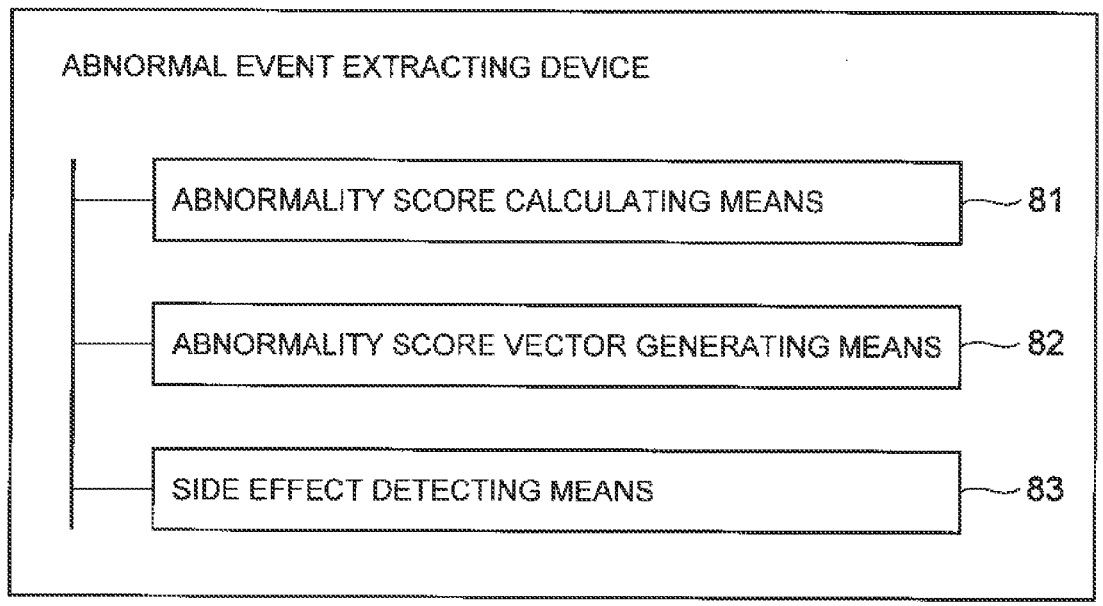
FIG. 13 It depicts a block diagram illustrating an example of a minimum configuration of a device which extracts an abnormal event from medical information according to this invention.

Next, an example of a minimum configuration of a device (referred to simply as "abnormal event extracting device" below) which extracts an abnormal event from medical information according to this invention will be described. FIG. 13 is a block diagram illustrating an example of a minimum configuration of the abnormal event extracting device according to this invention. The abnormal event extracting device (for example, the side effect detecting device 100) according to this invention has: the abnormality score calculating means 81 (for example, the abnormality detecting means) which calculates an abnormality score (for example, an abnormality score smk) which is information indicating abnormality of medical data (for example, the data xn) based on specificity of each medical data; the abnormality score vector generating means 82 (for example, the abnormality score integrating means 115) which creates at least one or more abnormality score vectors (for example, the abnormality score vector wi) which are information obtained by integrating abnormality scores; and the side effect detecting means 83 (for example, the side effect detecting means 104) which decides a likelihood of a side effect indicated by the abnormality score vector (for example, whether or not a side effect occurs) based on a predetermined rule (for example, a weighted sum of abnormality scores, a classification model or a regression model), and detects an abnormality score vector the likelihood of which satisfies conditions set in advance (for example, a predetermined threshold, or a learning result of a classification model or a regression model) as information indicating a side effect.

According to this configuration, it is possible to extract an unknown side effect of a drug from information related to medical treatment.

Further, the abnormal event extracting device may have a characteristics extracting means (for example, the characteristics extracting means 201) which extracts characteristics of the abnormality score vector detected as information indicating a side effect or medical data specified based on this abnormality score vector. According to this configuration, it is possible to provide information which is useful to analyze an unknown side effect to users.

Further, the abnormal event extracting device may have a feedback information input means (for example, the feedback input device 306) which receives an input of feedback information (for example, the feedback information 307) which is information used to analyze a side effect. Furthermore, the feedback information input means may receive as feedback information an input of at least one of information used to calculate abnormality scores (for example, information which has already been analyzed or a processing method of calculating abnormality scores), information used to create an abnormality score vector (for example, whether or not a side effect occurs or seriousness information) and information used to detect a side effect (for example, information which has already been analyzed or information indicating a view point of detecting a side effect), when receiving an input of information used to calculate abnormality scores as feedback information, the abnormality score calculating means 81 may calculate the abnormality scores based on this information, when receiving an input of information used to create an abnormality score vector as feedback information, the abnormality score vector generating means 82 may create the abnormality score vector based on this information, and when receiving an input of information used to detect a side effect as feedback information, the side effect detecting means 83 may detect a side effect based on this information.

Still further, the feedback information input means may receive as feedback information an input of information used to extract characteristics (for example, information which has already been analyzed or a processing method of extracting a characteristic element from input information), and, when receiving an input of information used to extract characteristics as feedback information, the characteristics extracting means may extract characteristics based on this information.

Moreover, the feedback information input means may receive an input of information indicating new processing of detecting abnormality scores as information used to calculate abnormality scores, and, when receiving an input of this processing as feedback information, the abnormality score calculating means 81 may calculate abnormality scores based on this processing.

Further, the abnormality event extracting device may have a side effect integrating means (for example, the side effect detection result integrating means 125) which integrates a plurality of pieces of information indicating a side effect. Furthermore, the abnormality score vector generating means 82 may generate a plurality of abnormality score vectors (for example, the abnormality score vector 1_121 to the abnormality score vector L_122), the side effect detecting means 83 (for example, the side effect detecting means 1_123 to the side effect detecting means L_124) may decide a likelihood of a side effect per abnormality score vector based on at least one or more types of rules, and the side effect integrating means may integrate abnormality score vectors detected as information indicating a side effect by the side effect detecting means 83 (for example, generate a final side effect detection result based on L decision values).

Still further, the abnormality score calculating means 81 may extract specific medical data from medical data of the same kind by using the outlier detecting method or the change point detecting method (for a longitudinal time series data or a plurality of items of cross-sectional data).

Moreover, the side effect detecting means 83 may label an abnormality score vector based on medical data linked to this abnormality score vector, learns a classification model for deciding a likelihood of a side effect using the labeled abnormality score vector, and detect the abnormality score vector classified as information indicating the side effect using this classification model.

Although part or all of the above exemplary embodiments are described as the following supplementary notes, part or all of the above exemplary embodiments are not limited to below.

(Supplementary note 1) A device which extracts an abnormal event from medical information has: an abnormality score calculating means which calculates an abnormality score which is information indicating abnormality of medical data, based on specificity of the medical data; an abnormality score vector generating means which creates at least one or more abnormality score vectors which are information obtained by integrating the abnormality score; and a side effect detecting means which decides a likelihood of a side effect indicated by the abnormality score vector, based on a predetermined rule, and detects an abnormality score vector the likelihood of which satisfies a condition set in advance as information indicating the side effect.

(Supplementary note 2) The abnormal event extracting device according to supplementary note 1 has a characteristics extracting means which extracts characteristics of the abnormality score vector detected as the information indicating the side effect or medical data specified based on the abnormality score vector.

(Supplementary note 3) The abnormal event extracting device according to supplementary note 1 or supplementary note 2, has a feedback information input means which receives an input of feedback information which is information used to analyze the side effect, and the feedback information input means receives as feedback information an input of at least one of information used to calculate the abnormality score, information used to create the abnormality score vector and information used to detect the side effect, when receiving an input of the information used to calculate the abnormality score as the feedback information, the abnormality score calculating means calculates the abnormality score based on the information, when receiving an input of the information used to create the abnormality score vector as the feedback information, the abnormality score vector generating means creates the abnormality score vector based on the information, and when receiving an input of the information used to detect the side effect as the feedback information, the side effect detecting means detects the side effect based on the information.

(Supplementary note 4) In the abnormal event extracting device according to supplementary note 3, the feedback information input means receives an input of information used to extract the characteristics as the feedback information, and when receiving an input of the information used to extract the characteristics as the feedback information, the characteristics extracting means extracts the characteristics based on the information.

(Supplementary note 5) In the abnormal event extracting device according to supplementary note 3 or supplementary note 4, the feedback information input means receives an input of information indicating new processing of detecting the abnormality score as information used to calculate the abnormality score, and when receiving an input of the processing as the feedback information, the abnormality score calculating means calculates the abnormality score based on the processing.

(Supplementary note 6) The abnormal event extracting device according to any one of supplementary note 1 to supplementary note 5 further has a side effect integrating means which integrates a plurality of pieces of information indicating the side effect, and the abnormality score vector generating means generates a plurality of abnormality score vectors, the side effect detecting means decides a likelihood of a side effect per abnormality score vector based on at least one type or more rules, and the side effect integrating means integrates the abnormality score vectors detected as the information indicating the side effect by the side effect detecting means.

(Supplementary note 7) In the abnormal event extracting device according to any one of supplementary note 1 to supplementary note 6, the abnormality score calculating means extracts specific medical data from medical data of the same kind by using an outlier detecting method or a change point detecting method.

(Supplementary note 8) In the abnormal event extracting device according to any one of supplementary note 1 to supplementary note 7, the side effect detecting means labels an abnormality score vector based on medical data linked to the abnormality score vector, learns a classification model for deciding a likelihood of the side effect using the labeled abnormality score vector and detects the abnormality score vector classified as information indicating the side effect using the classification model.

(Supplementary note 9) In the abnormal event extracting device according to any one of supplementary note 1 to supplementary note 6, the abnormality score calculating means extracts specific information by deciding whether or not the specific information matches with a predetermined rule.

(Supplementary note 10) A method of extracting an abnormal event from medical information includes: calculating an abnormality score which is information indicating abnormality of medical data, based on specificity of the medical data; creating at least one or more abnormality score vectors which are information obtained by integrating the abnormality score; and deciding a likelihood of a side effect indicated by the abnormality score vector, based on a predetermined rule, and detecting an abnormality score vector the likelihood of which satisfies a condition set in advance as information indicating the side effect.

(Supplementary note 11) The abnormal event extracting method according to supplementary note 10 includes extracting characteristics of the abnormality score vector detected as the information indicating the side effect or medical data specified based on the abnormality score vector.

(Supplementary note 12) A program of extracting an abnormal event from medical information causes the computer to execute: abnormality score calculation processing of calculating an abnormality score which is information indicating abnormality of medical data, based on specificity of the medical data; abnormality score vector generation processing of creating at least one or more abnormality score vectors which are information obtained by integrating the abnormality score; and side effect detection processing of deciding a likelihood of a side effect indicated by the abnormality score vector, based on a predetermined rule, and detecting an abnormality score vector the likelihood of which satisfies a condition set in advance as information indicating the side effect.

(Supplementary note 13) The abnormal event extracting program according to supplementary note 12 causes the computer to execute characteristics extraction processing of extracting characteristics of the abnormality score vector detected as the information indicating the side effect or medical data specified based on the abnormality score vector.

Although this invention has been described with reference to the exemplary embodiments and the examples, this invention is by no means limited to the above exemplary embodiments and examples. The configurations and the details of this invention can be variously modified within a scope of this invention which one of ordinary skill in art can understand.

This application claims priority to Japanese Patent Application No. 2010-146680 filed on Jun. 28, 2010, the entire contents of which are incorporated by reference herein.

INDUSTRIAL APPLICABILITY

This invention is suitably applied to an abnormal event extracting device which extracts an abnormal event from medical information.

REFERENCE SIGNS LIST 100, 200, 300 Side effect detecting device
101 Input device
102 Input data memory unit
103 Abnormality score vector generating means
104 Side effect detecting means
105, 202 Output device
108 Extended side effect detecting means
111, 112 Abnormality detecting means
115 Abnormality score integrating means
123, 124 Side effect detecting means
125 Side effect detection result integrating means
201 Characteristics extracting means
301 Abnormality score vector generating means
302 Extended side effect detecting means
303 Extended characteristics extracting means
304 Side effect detection result memory unit
305 Feedback memory unit
306 Feedback input device
311 First feedback reflecting means
321 Second feedback reflecting means
331 Third feedback reflecting means

The invention claimed is:

1. A device which has a processor for implementing units and extracts an abnormal event from medical information comprising:
   an abnormality score calculating unit implemented by the processor which calculates an abnormality score which is information indicating abnormality of medical data, based on specificity of the medical data;
   an abnormality score vector generating unit implemented by the processor which creates at least one or more abnormality score vectors of which the calculated abnormality scores are each component; and
   a side effect detecting unit, implemented by the processor which decides a likelihood of a side effect indicated by the abnormality score vector, based on a predetermined rule, and detects an abnormality score vector the likelihood of which satisfies a condition set in advance as information indicating the side effect, and identifies medical data corresponding to the abnormality scores from the detected abnormality score vector, wherein side effect information indicating whether or not a side effect occurs is set to part or all of the medical information,
   wherein the abnormality score vector generating unit sets a label indicating whether or not a side effect occurs to the abnormality score vector which is created based on the medical information where the side effect information is set, and
   wherein the side effect detecting unit learns a classification model for deciding whether or not a side effect occurs using the labeled abnormality score vector.

2. The abnormal event extracting device according to claim 1, further comprising a characteristics extracting unit implemented by the processor which extracts characteristics of the abnormality score vector detected as the information indicating the side effect or medical data specified based on the abnormality score vector.

3. The abnormal event extracting device according to claim 1, further comprising a feedback information input unit implemented by the processor which receives an input of feedback information which is information used to analyze the side effect, wherein:
   the feedback information input unit receives as feedback information an input of at least one of information used to calculate the abnormality score, information used to create the abnormality score vector and information used to detect the side effect;
   when receiving an input of the information used to calculate the abnormality score as the feedback information, the abnormality score calculating unit calculates the abnormality score based on the information;
   when receiving an input of the information used to create the abnormality score vector as the feedback information, the abnormality score vector generating unit creates the abnormality score vector based on the information; and when receiving an input of the information used to detect the side effect as the feedback information, the side effect detecting unit detects the side effect based on the information.

4. The abnormal event extracting device according to claim 3, wherein:

the feedback information input unit receives an input of information used to extract the characteristics as the feedback information; and when receiving an input of the information used to extract the characteristics as the feedback information, the characteristics extracting unit extracts the characteristics based on the information.

5. The abnormal event extracting device according to claim 3, wherein:

the feedback information input unit receives an input of information indicating new processing of detecting the abnormality score as information used to calculate the abnormality score; and when receiving an input of the processing as the feedback information, the abnormality score calculating unit calculates the abnormality score based on the processing.

6. The abnormality event extracting device according to claim 1, further comprising a side effect integrating unit implemented by the processor which integrates a plurality of pieces of information indicating the side effect, wherein:

the abnormality score vector generating unit generates a plurality of abnormality score vectors;

the side effect detecting unit decides a likelihood of a side effect per abnormality score vector based on at least one type or more rules; and the side effect integrating unit integrates the abnormality score vectors detected as the information indicating the side effect by the side effect detecting unit.

7. The abnormal event extracting device according to claim 1, wherein the abnormality score calculating unit extracts specific medical data from medical data of the same kind by using an outlier detecting method or a change point detecting method.

8. The abnormal event extracting device according to claim 1, wherein the side effect detecting unit labels an abnormality score vector based on medical data linked to the abnormality score vector, learns a classification model for deciding a likelihood of the side effect using the labeled abnormality score vector and detects the abnormality score vector classified as information indicating the side effect using the classification model.

9. The abnormal event extracting device according to claim 1, wherein the side effect detecting unit decides whether or not a side effect of an abnormality score vector which is not labeled using the learned classification model.

10. A method of extracting an abnormal event from medical information, the method comprising:

calculating an abnormality score which is information indicating abnormality of medical data, based on specificity of the medical data;

creating at least one or more abnormality score vectors of which the calculated abnormality scores are each component; and deciding a likelihood of a side effect indicated by the abnormality score vector, based on a predetermined rule, and detecting an abnormality score vector the likelihood of which satisfies a condition set in advance as information indicating the side effect, and identifying medical data corresponding to the abnormality scores from the detected abnormality score vector, wherein side effect information indicating whether or not a side effect occurs is set to part or all of the medical information, wherein creatin the abnormality score vector sets a label indicating whether or not a side effect occurs to the abnormality score vector which is created based on the medical information where the side effect information is set, and wherein the deciding the likelihood of the side effect is based on learning that a classification model for deciding whether or not a side effect occurs using the labeled abnormality score vector.

11. A non-transitory computer readable information recording medium storing a program causing a computer to execute a method of extracting an abnormal event from medical information, when executed by a processor, the method comprising:

calculating an abnormality score which is information indicating abnormality of medical data, based on specificity of the medical data;

creating at least one or more abnormality score vectors of which the calculated abnormality scores are each component; and deciding a likelihood of a side effect indicated by the abnormality score vector, based on a predetermined rule, and detecting an abnormality score vector the likelihood of which satisfies a condition set in advance as information indicating the side effect, and identifying medical data corresponding to the abnormality scores from the detected abnormality score vector, wherein side effect information indicating whether or not a side effect occurs is set to part or all of the medical information, wherein creating the abnormality score vector sets a label indicating whether or not a side effect occurs to the abnormality score vector which is created based on the medical information where the side effect information is set, and wherein the deciding the likelihood of the side effect is based on learning that a classification model for deciding whether or not a side effect occurs using the labeled abnormality score vector.

* * * * *